US012376901B2

(12) United States Patent
Sutermeister et al.

(10) Patent No.: US 12,376,901 B2
(45) Date of Patent: Aug. 5, 2025

(54) RADIO-FREQUENCY ABLATION AND DIRECT CURRENT ELECTROPORATION CATHETERS

(71) Applicant: St. Jude Medical, Cardiology Division, Inc., St. Paul, MN (US)

(72) Inventors: Derek C. Sutermeister, Ham Lake, MN (US); Troy T. Tegg, Elk River, MN (US); Salo Arias, Brooklyn Park, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 354 days.

(21) Appl. No.: 17/502,902

(22) Filed: Oct. 15, 2021

(65) Prior Publication Data
US 2022/0175445 A1 Jun. 9, 2022

Related U.S. Application Data

(63) Continuation of application No. 16/418,296, filed on May 21, 2019, now abandoned.
(Continued)

(51) Int. Cl.
*A61B 18/14* (2006.01)
*A61B 5/00* (2006.01)
(Continued)

(52) U.S. Cl.
CPC .......... *A61B 18/1492* (2013.01); *A61B 5/287* (2021.01); *A61B 5/6858* (2013.01);
(Continued)

(58) Field of Classification Search
CPC ...... A61B 18/1492; A61B 2017/00053; A61B 2017/00092; A61B 2017/00101;
(Continued)

(56) References Cited

U.S. PATENT DOCUMENTS

| 4,522,212 A | 6/1985 | Gelinas et al. |
| 5,224,939 A | 7/1993 | Holman et al. |

(Continued)

FOREIGN PATENT DOCUMENTS

| AU | 2015202258 A1 | 5/2015 |
| AU | 2015202258 B2 | 6/2016 |

(Continued)

OTHER PUBLICATIONS

Magtibay et al., JAHA 2017 (J Am Heart Assoc. 2017;6:e006447. DOI: 10.1161/JAHA. 117.006447). pp. 6-7, and section titled "Omnipoles Provide the Largest Possible Bipolar Voltages".
(Continued)

*Primary Examiner* — Michael F Peffley
(74) *Attorney, Agent, or Firm* — Kilpatrick Townsend & Stockton LLP

(57) ABSTRACT

Aspects of the present disclosure are directed to flexible catheters for both electrophysiology mapping and ablation using a high-density array of electrodes. These catheters may be used to detect electrophysiological characteristics of tissue in contact with the electrodes, and conduct monopolar and bipolar ablations of the tissue.

18 Claims, 6 Drawing Sheets

Related U.S. Application Data

(60) Provisional application No. 62/674,314, filed on May 21, 2018.

(51) Int. Cl.
*A61B 5/287* (2021.01)
*A61B 18/00* (2006.01)

(52) U.S. Cl.
CPC ............ *A61B 2018/00267* (2013.01); *A61B 2018/00351* (2013.01); *A61B 2018/00577* (2013.01); *A61B 2018/00613* (2013.01); *A61B 2018/00839* (2013.01); *A61B 2018/1405* (2013.01); *A61B 2018/1467* (2013.01); *A61B 2562/0209* (2013.01)

(58) Field of Classification Search
CPC ........... A61B 2017/00243; A61B 2017/00867; A61B 2018/0016; A61B 2018/00267; A61B 2018/00351; A61B 2018/00357; A61B 2018/00363; A61B 2018/00577; A61B 2018/00613; A61B 2018/00797; A61B 2018/00839; A61B 2018/1405; A61B 2018/1467; A61B 2034/2051; A61B 2034/2053; A61B 2505/05; A61B 2562/0209; A61B 2562/0271; A61B 5/01; A61B 5/287; A61B 5/361; A61B 5/4848; A61B 5/6858; A61B 5/6859; A61N 1/056
See application file for complete search history.

(56) References Cited

U.S. PATENT DOCUMENTS

| | | | |
|---|---|---|---|
| 5,380,301 A | 1/1995 | Prichard et al. | |
| 5,400,783 A | 3/1995 | Pomeranz et al. | |
| 5,456,254 A | 10/1995 | Pietroski et al. | |
| 5,626,136 A | 5/1997 | Webster, Jr. | |
| 5,702,438 A | 12/1997 | Avitall | |
| 5,715,817 A | 2/1998 | Stevens-Wright et al. | |
| 5,715,832 A | 2/1998 | Koblish et al. | |
| 5,782,239 A | 7/1998 | Webster, Jr. | |
| 5,827,278 A | 10/1998 | Webster, Jr. | |
| 5,876,373 A | 3/1999 | Giba et al. | |
| 5,964,757 A | 10/1999 | Ponzi | |
| 6,015,405 A | 1/2000 | Schwartz et al. | |
| 6,029,091 A * | 2/2000 | de la Rama | A61B 18/1492 607/148 |
| 6,071,282 A | 6/2000 | Fleischman | |
| 6,074,379 A | 6/2000 | Prichard | |
| 6,123,699 A | 9/2000 | Webster, Jr. | |
| 6,171,277 B1 | 1/2001 | Ponzi | |
| 6,183,463 B1 | 2/2001 | Webster, Jr. | |
| 6,198,974 B1 | 3/2001 | Webster, Jr. | |
| 6,210,407 B1 | 4/2001 | Webster | |
| 6,267,746 B1 | 7/2001 | Bumbalough | |
| 6,273,404 B1 | 8/2001 | Holman et al. | |
| 6,415,187 B1 | 7/2002 | Kuzma et al. | |
| 6,491,681 B1 | 12/2002 | Kunis et al. | |
| 6,522,932 B1 | 2/2003 | Kuzma et al. | |
| 6,554,794 B1 | 4/2003 | Mueller et al. | |
| 6,652,515 B1 | 11/2003 | Maguire et al. | |
| 6,658,302 B1 | 12/2003 | Kuzma et al. | |
| 6,961,602 B2 | 11/2005 | Fuimaono et al. | |
| 7,004,937 B2 | 2/2006 | Lentz et al. | |
| 7,027,851 B2 | 4/2006 | Mejia | |
| 7,089,045 B2 | 8/2006 | Fuimaono et al. | |
| 7,099,712 B2 | 8/2006 | Fuimaono et al. | |
| 7,214,220 B2 | 5/2007 | McGlinch et al. | |
| 7,217,256 B2 | 5/2007 | Di Palma | |
| 7,228,164 B2 | 6/2007 | Fuimaono et al. | |
| 7,257,435 B2 | 8/2007 | Plaza | |
| 7,412,274 B2 | 8/2008 | Mejia | |
| 7,429,261 B2 | 9/2008 | Kunis et al. | |
| 7,561,907 B2 | 7/2009 | Fuimaono et al. | |
| 7,608,063 B2 | 10/2009 | Le et al. | |
| 7,625,365 B2 | 12/2009 | McGlinch et al. | |
| 7,666,204 B2 | 2/2010 | Thornton et al. | |
| 7,853,333 B2 * | 12/2010 | Demarais | A61B 18/1492 607/118 |
| 7,959,601 B2 | 6/2011 | McDaniel et al. | |
| 7,985,215 B2 | 7/2011 | Guo et al. | |
| 8,103,327 B2 | 1/2012 | Harlev et al. | |
| 8,137,321 B2 | 3/2012 | Argentine | |
| 8,157,848 B2 | 4/2012 | Zhang et al. | |
| 8,221,390 B2 | 7/2012 | Pal et al. | |
| 8,271,099 B1 | 8/2012 | Swanson | |
| 8,273,016 B2 | 9/2012 | O'Sullivan | |
| 8,376,990 B2 | 2/2013 | Ponzi et al. | |
| 8,391,947 B2 | 3/2013 | Urman et al. | |
| 8,447,377 B2 | 5/2013 | Harlev et al. | |
| 8,486,063 B2 * | 7/2013 | Werneth | A61B 18/1492 606/41 |
| 8,565,894 B2 | 10/2013 | Vetter et al. | |
| 8,603,069 B2 | 12/2013 | Selkie | |
| 8,608,703 B2 | 12/2013 | Riles et al. | |
| 8,649,880 B1 | 2/2014 | Parker, Jr. | |
| 8,700,120 B2 | 4/2014 | Koblish | |
| 8,706,193 B2 | 4/2014 | Govari et al. | |
| 8,744,599 B2 | 6/2014 | Tegg | |
| 8,755,861 B2 | 6/2014 | Harlev et al. | |
| 8,771,267 B2 | 7/2014 | Kunis et al. | |
| 8,777,929 B2 | 7/2014 | Schneider et al. | |
| 8,792,962 B2 | 7/2014 | Esguerra et al. | |
| 8,814,824 B2 | 8/2014 | Kauphusman et al. | |
| 8,814,825 B2 | 8/2014 | Tegg et al. | |
| 8,882,705 B2 | 11/2014 | McDaniel et al. | |
| 8,894,610 B2 | 11/2014 | Macnamara et al. | |
| 8,979,841 B2 | 3/2015 | Kunis et al. | |
| 8,996,091 B2 | 3/2015 | de la Rama et al. | |
| 9,017,308 B2 | 4/2015 | Klisch et al. | |
| 9,033,917 B2 | 5/2015 | Magana et al. | |
| 9,044,245 B2 | 6/2015 | Condie et al. | |
| 9,050,010 B2 | 6/2015 | Bui et al. | |
| 9,101,733 B2 | 8/2015 | McDaniel | |
| 9,204,929 B2 | 12/2015 | Solis | |
| 9,216,056 B2 | 12/2015 | Datta et al. | |
| 9,247,990 B2 | 2/2016 | Kauphusman et al. | |
| 9,326,815 B2 | 5/2016 | Watson | |
| 9,339,631 B2 | 5/2016 | Graham et al. | |
| 9,433,751 B2 | 9/2016 | Ponzi et al. | |
| 9,433,752 B2 | 9/2016 | Jimenez et al. | |
| 9,468,495 B2 | 10/2016 | Kunis et al. | |
| 9,486,280 B2 | 11/2016 | Koblish et al. | |
| 9,486,282 B2 | 11/2016 | Solis | |
| 9,522,035 B2 | 12/2016 | Highsmith | |
| 9,532,703 B2 | 1/2017 | Huszar et al. | |
| 9,539,413 B2 | 1/2017 | Ogle | |
| 9,629,675 B2 | 4/2017 | Kleshinski et al. | |
| 9,649,158 B2 | 5/2017 | Datta et al. | |
| 9,687,166 B2 | 6/2017 | Subramaniam et al. | |
| 9,693,733 B2 | 7/2017 | Altmann et al. | |
| 9,694,159 B2 | 7/2017 | Schneider et al. | |
| 9,694,161 B2 | 7/2017 | Selkee | |
| 9,713,418 B2 | 7/2017 | Huszar et al. | |
| 9,788,895 B2 | 10/2017 | Solis | |
| 9,820,664 B2 | 11/2017 | Hoitink et al. | |
| 9,833,608 B2 | 12/2017 | Masson | |
| 9,844,645 B2 | 12/2017 | Pai et al. | |
| 9,848,795 B2 | 12/2017 | Marecki et al. | |
| 9,907,480 B2 | 3/2018 | Basu et al. | |
| 9,919,132 B2 | 3/2018 | Tegg et al. | |
| 9,949,656 B2 | 4/2018 | Wu et al. | |
| 9,986,949 B2 | 6/2018 | Govari et al. | |
| 10,004,877 B2 | 6/2018 | Tegg | |
| 10,034,637 B2 | 7/2018 | Harlev et al. | |
| 10,052,457 B2 | 8/2018 | Nguyen et al. | |
| 10,065,019 B2 | 9/2018 | Hamuro et al. | |
| 10,099,036 B2 | 10/2018 | Heideman et al. | |
| 10,118,022 B2 | 11/2018 | Helgeson et al. | |
| 10,136,829 B2 | 11/2018 | Deno et al. | |
| 10,143,394 B2 | 12/2018 | Solis | |
| 10,285,610 B2 | 5/2019 | Wu | |

(56) References Cited

U.S. PATENT DOCUMENTS

| | | |
|---|---|---|
| 10,322,261 B2 | 6/2019 | Pai et al. |
| 10,362,952 B2 | 7/2019 | Basu et al. |
| 10,362,954 B2 | 7/2019 | de la Rama et al. |
| 10,376,170 B2 | 8/2019 | Quinn et al. |
| 10,384,036 B2 | 8/2019 | Romoscanu |
| 10,398,500 B2 | 9/2019 | Huszar et al. |
| 10,470,682 B2 | 11/2019 | Deno et al. |
| 10,478,247 B2 | 11/2019 | Litscher et al. |
| 10,478,325 B2 | 11/2019 | Syed |
| 10,506,938 B2 | 12/2019 | Wu et al. |
| 10,537,259 B2 | 1/2020 | Wu et al. |
| 10,542,899 B2 | 1/2020 | Wu et al. |
| 10,556,091 B2 | 2/2020 | Truhler et al. |
| 10,575,742 B2 | 3/2020 | Wu et al. |
| 10,575,745 B2 | 3/2020 | Solis |
| 10,578,737 B2 | 3/2020 | Gliner et al. |
| 10,595,738 B2 | 3/2020 | Sterrett et al. |
| 10,595,740 B2 | 3/2020 | Hoitink et al. |
| 10,602,948 B2 | 3/2020 | Wu et al. |
| 10,646,692 B2 | 5/2020 | Tegg et al. |
| 10,653,423 B2 | 5/2020 | Starnes |
| 10,702,177 B2 | 7/2020 | Aujla |
| 10,702,677 B2 | 7/2020 | Okamura et al. |
| 10,737,060 B2 | 8/2020 | Gupta et al. |
| 10,813,590 B2 | 10/2020 | Ruppersberg |
| 10,835,712 B2 | 11/2020 | Wada |
| 10,842,990 B2 | 11/2020 | de la Rama et al. |
| 10,857,349 B2 | 12/2020 | de la Rama et al. |
| 10,869,992 B2 | 12/2020 | Pai et al. |
| 10,898,685 B2 | 1/2021 | Tegg |
| 10,905,347 B2 | 2/2021 | Fuentes-Ortega et al. |
| 10,912,925 B2 | 2/2021 | Houck |
| 10,945,626 B2 | 3/2021 | Fuentes-ortega et al. |
| 10,953,196 B2 | 3/2021 | Raab et al. |
| 10,959,636 B2 | 3/2021 | Dahlen et al. |
| 10,966,623 B2 | 4/2021 | Wu et al. |
| 10,966,753 B2 | 4/2021 | Coyle et al. |
| 10,967,150 B2 | 4/2021 | Helgeson et al. |
| 10,987,045 B2 | 4/2021 | Basu et al. |
| 11,033,715 B2 | 6/2021 | Beeckler et al. |
| 11,039,772 B2 | 6/2021 | Wu et al. |
| 11,039,773 B2 | 6/2021 | Sterrett et al. |
| 11,083,400 B2 | 8/2021 | Hoitink et al. |
| 11,116,436 B2 | 9/2021 | Wu et al. |
| 11,116,476 B2 | 9/2021 | Buesseler et al. |
| 11,123,051 B2 | 9/2021 | Van Der Linde et al. |
| 11,141,568 B2 | 10/2021 | Hsueh et al. |
| 11,160,482 B2 | 11/2021 | Solis |
| 11,172,858 B2 | 11/2021 | Olson et al. |
| 11,272,886 B2 | 3/2022 | Harlev et al. |
| 11,382,690 B2 | 7/2022 | Smith et al. |
| 11,382,743 B2 | 7/2022 | Marchand et al. |
| 11,383,078 B2 | 7/2022 | de la Rama et al. |
| 11,419,673 B2 | 8/2022 | Kauphusman et al. |
| 11,426,111 B2 | 8/2022 | Olson |
| 11,433,220 B2 | 9/2022 | Oliverius et al. |
| 11,439,460 B2 | 9/2022 | Sliwa et al. |
| 11,446,471 B2 | 9/2022 | Grunewald |
| 11,478,299 B2 | 10/2022 | Webster et al. |
| 11,484,690 B2 | 11/2022 | Tegg et al. |
| 11,491,311 B2 | 11/2022 | Selkee |
| 11,504,205 B2 | 11/2022 | Brucker et al. |
| 11,511,078 B2 | 11/2022 | Gonzalez |
| 11,517,715 B2 | 12/2022 | Govari |
| 11,523,748 B2 | 12/2022 | Esguerra Wilczynski et al. |
| 11,547,437 B2 | 1/2023 | Zarembinski |
| 11,583,334 B2 | 2/2023 | Caples et al. |
| 11,602,630 B2 | 3/2023 | Vetter et al. |
| 11,617,616 B2 | 4/2023 | Clark et al. |
| 11,617,859 B2 | 4/2023 | Hsueh et al. |
| 11,617,861 B2 | 4/2023 | Pai et al. |
| 11,622,806 B2 | 4/2023 | Romoscanu |
| 11,628,009 B2 | 4/2023 | Aujla |
| 11,660,119 B2 | 5/2023 | Hassett |
| 11,672,947 B2 | 6/2023 | Tegg et al. |
| 11,786,301 B2 | 10/2023 | Olson |
| 11,806,152 B2 | 11/2023 | Zeidan et al. |
| 11,813,410 B2 | 11/2023 | Olson et al. |
| 11,857,250 B2 | 1/2024 | Corvi et al. |
| 11,938,316 B2 | 3/2024 | Feler et al. |
| 2001/0007071 A1 | 7/2001 | Koblish et al. |
| 2002/0165484 A1 | 11/2002 | Bowe et al. |
| 2005/0159741 A1 | 7/2005 | Paul et al. |
| 2006/0089637 A1 | 4/2006 | Werneth et al. |
| 2007/0083194 A1 | 4/2007 | Kunis et al. |
| 2008/0281391 A1 | 11/2008 | Macadam et al. |
| 2008/0294158 A1 | 11/2008 | Pappone |
| 2009/0012517 A1 | 1/2009 | de la Rama |
| 2009/0149848 A1 | 6/2009 | Werneth et al. |
| 2009/0198300 A1 | 8/2009 | Zhang et al. |
| 2010/0152731 A1 | 6/2010 | De La Rama |
| 2010/0174177 A1 | 7/2010 | Wu |
| 2010/0286684 A1 | 11/2010 | Hata |
| 2011/0118582 A1 | 5/2011 | de la Rama |
| 2011/0118726 A1 | 5/2011 | de la Rama et al. |
| 2011/0230775 A1 | 9/2011 | Barley et al. |
| 2011/0288392 A1 | 11/2011 | de la Rama |
| 2011/0313417 A1 | 12/2011 | de la Rama |
| 2012/0010490 A1 | 1/2012 | Kauphusman |
| 2012/0197100 A1 | 8/2012 | Razavi et al. |
| 2012/0271302 A1 | 10/2012 | Behl et al. |
| 2012/0296232 A1 | 11/2012 | Ng |
| 2013/0085479 A1 | 4/2013 | de la Rama |
| 2013/0190747 A1 | 7/2013 | Koblish et al. |
| 2013/0253504 A1 | 9/2013 | Fang |
| 2013/0274582 A1 | 10/2013 | Afonso et al. |
| 2014/0100639 A1 | 4/2014 | Lee et al. |
| 2014/0200639 A1 | 7/2014 | de la Rama |
| 2014/0269602 A1 | 9/2014 | Kawagishi |
| 2014/0296846 A1 | 10/2014 | Huszar et al. |
| 2014/0296902 A1 | 10/2014 | Huszar et al. |
| 2014/0316496 A1 | 10/2014 | Masson et al. |
| 2014/0336636 A1 | 11/2014 | Huszar et al. |
| 2014/0350564 A1 | 11/2014 | Huszar et al. |
| 2015/0001191 A1 | 1/2015 | Lee et al. |
| 2015/0105645 A1 | 4/2015 | Subramaniam et al. |
| 2015/0119911 A1 | 4/2015 | Mckenzie |
| 2015/0141785 A1 | 5/2015 | Hayam et al. |
| 2015/0159741 A1 | 6/2015 | Versteyhe et al. |
| 2015/0351652 A1 | 12/2015 | Marecki et al. |
| 2015/0366508 A1 | 12/2015 | Chou et al. |
| 2015/0374252 A1 | 12/2015 | de la Rama |
| 2016/0143588 A1 | 5/2016 | Hoitink et al. |
| 2016/0213423 A1 | 7/2016 | Kauphusman et al. |
| 2016/0213916 A1 | 7/2016 | de la Rama |
| 2016/0278660 A1* | 9/2016 | Nagale ................ A61B 5/202 |
| 2016/0278851 A1 | 9/2016 | Mannion et al. |
| 2016/0317094 A1 | 11/2016 | Byrd et al. |
| 2016/0331471 A1 | 11/2016 | Deno et al. |
| 2016/0331933 A1 | 11/2016 | Knutsen |
| 2016/0374582 A1 | 12/2016 | Wu et al. |
| 2016/0374753 A1 | 12/2016 | Wu et al. |
| 2017/0000365 A1 | 1/2017 | Wu et al. |
| 2017/0035496 A1 | 2/2017 | Nagale et al. |
| 2017/0042449 A1 | 2/2017 | Deno |
| 2017/0049348 A1* | 2/2017 | Deno .................... A61B 5/339 |
| 2017/0065273 A1 | 3/2017 | Mickelsen |
| 2017/0112404 A1* | 4/2017 | de la Rama ......... A61B 5/6858 |
| 2017/0112405 A1* | 4/2017 | Sterrett ................ H05K 3/06 |
| 2017/0143414 A1 | 5/2017 | Sliwa et al. |
| 2017/0231683 A1 | 8/2017 | Weinkam et al. |
| 2017/0273738 A1 | 9/2017 | Wu |
| 2017/0319269 A1* | 11/2017 | Oliverius ........... A61B 18/1492 |
| 2017/0367756 A1 | 12/2017 | Sliwa et al. |
| 2018/0042667 A1* | 2/2018 | Pappone ................. A61F 7/12 |
| 2018/0050190 A1 | 2/2018 | Masson |
| 2018/0056038 A1 | 3/2018 | Aujla |
| 2018/0070845 A1 | 3/2018 | Hoitink et al. |
| 2018/0085064 A1 | 3/2018 | Auerbach et al. |
| 2018/0116539 A1* | 5/2018 | Olson ................. A61B 5/6858 |
| 2018/0161093 A1 | 6/2018 | Basu et al. |
| 2018/0193089 A1 | 7/2018 | Wu |
| 2018/0229030 A1 | 8/2018 | Dubuclet et al. |
| 2018/0235496 A1 | 8/2018 | Wu et al. |

(56) References Cited

U.S. PATENT DOCUMENTS

| | | |
|---|---|---|
| 2018/0303361 A1 | 10/2018 | Wu et al. |
| 2018/0335519 A1 | 11/2018 | Gliner et al. |
| 2018/0369574 A1 | 12/2018 | Dubuclet et al. |
| 2019/0009052 A1 | 1/2019 | Oliverius et al. |
| 2019/0125378 A1 | 5/2019 | Shelton, IV et al. |
| 2019/0175043 A1 | 6/2019 | Wu et al. |
| 2019/0192826 A1 | 6/2019 | Wada |
| 2019/0239812 A1 | 8/2019 | Botzer et al. |
| 2020/0054391 A1 | 2/2020 | Litscher et al. |
| 2020/0077912 A1 | 3/2020 | Wu et al. |
| 2020/0121894 A1 | 4/2020 | Prabhu et al. |
| 2020/0138378 A1 | 5/2020 | de La Rama et al. |
| 2020/0155021 A1 | 5/2020 | Wu et al. |
| 2020/0214635 A1 | 7/2020 | Dahlen et al. |
| 2020/0221966 A1 | 7/2020 | Wu et al. |
| 2020/0229727 A1 | 7/2020 | Hoitink et al. |
| 2020/0253496 A1 | 8/2020 | Deno et al. |
| 2020/0329989 A1 | 10/2020 | Aujla |
| 2020/0405166 A1 | 12/2020 | Wu et al. |
| 2021/0068693 A1 | 3/2021 | Fuentes-Ortega et al. |
| 2021/0145342 A1 | 5/2021 | Wang |
| 2021/0153932 A1 | 5/2021 | Voth et al. |
| 2021/0187246 A1 | 6/2021 | Houck |
| 2021/0204871 A1 | 7/2021 | Goedeke et al. |
| 2021/0228136 A1 | 7/2021 | Fuentes-Ortega et al. |
| 2021/0228137 A1 | 7/2021 | Aujla |
| 2021/0267693 A1 | 9/2021 | Deno et al. |
| 2021/0268234 A1 | 9/2021 | Helgeson et al. |
| 2021/0298656 A1 | 9/2021 | Wu et al. |
| 2021/0361216 A1 | 11/2021 | Hoitink et al. |
| 2021/0401345 A1 | 12/2021 | Wu et al. |
| 2022/0023594 A1 | 1/2022 | Pai |
| 2022/0054066 A1 | 2/2022 | Solis |
| 2022/0061727 A1 | 3/2022 | Olson et al. |
| 2022/0273913 A1 | 9/2022 | Worley et al. |
| 2022/0354568 A1 | 11/2022 | Pappone et al. |
| 2022/0370792 A1 | 11/2022 | de la Rama et al. |
| 2022/0387012 A1 | 12/2022 | Nunan |
| 2022/0401693 A1 | 12/2022 | Oliverius et al. |
| 2023/0000415 A1 | 1/2023 | Olson |
| 2023/0078216 A1 | 3/2023 | Govari |
| 2023/0084626 A1 | 3/2023 | Grunewald |
| 2023/0114222 A1 | 4/2023 | Esguerra Wilczynski et al. |
| 2023/0121397 A1 | 4/2023 | Oliverius et al. |
| 2023/0190369 A1 | 6/2023 | Caples et al. |
| 2023/0284956 A1 | 9/2023 | Wu et al. |
| 2023/0329618 A1 | 10/2023 | Wu et al. |
| 2023/0329784 A1 | 10/2023 | Stewart et al. |
| 2023/0404657 A1 | 12/2023 | Olson |
| 2024/0033470 A1 | 2/2024 | Olson et al. |
| 2024/0081905 A1 | 3/2024 | Corvi et al. |

FOREIGN PATENT DOCUMENTS

| | | |
|---|---|---|
| AU | 2016204351 A1 | 1/2017 |
| AU | 2016204353 A1 | 1/2017 |
| AU | 2016204355 A1 | 1/2017 |
| CA | 2934209 A1 | 12/2016 |
| CA | 2934211 A1 | 12/2016 |
| CA | 2934214 A1 | 12/2016 |
| CN | 101797181 A | 8/2010 |
| CN | 101927053 B | 1/2015 |
| CN | 103157168 B | 4/2015 |
| CN | 101797181 B | 12/2015 |
| CN | 106264715 A | 1/2017 |
| CN | 106264716 A | 1/2017 |
| CN | 106308790 A | 1/2017 |
| CN | 106859765 A | 6/2017 |
| CN | 106901831 A | 6/2017 |
| CN | 107405099 A | 11/2017 |
| CN | 206880930 U | 1/2018 |
| CN | 104958824 B | 12/2018 |
| CN | 104434083 B | 4/2019 |
| CN | 104968261 B | 5/2019 |
| CN | 105592778 B | 7/2019 |
| CN | 105960200 B | 8/2019 |
| CN | 105451680 B | 10/2019 |
| CN | 110536646 A | 12/2019 |
| CN | 105960201 B | 3/2020 |
| CN | 111225627 A | 6/2020 |
| CN | 111432739 A | 7/2020 |
| CN | 111657866 A | 9/2020 |
| CN | 106264715 B | 11/2020 |
| CN | 106264716 B | 11/2020 |
| CN | 112040861 A | 12/2020 |
| CN | 106308790 B | 6/2021 |
| CN | 107529958 B | 7/2021 |
| CN | 109310469 B | 7/2021 |
| CN | 109641121 B | 9/2021 |
| CN | 109952123 B | 9/2021 |
| CN | 110545874 B | 9/2021 |
| CN | 110559544 B | 9/2021 |
| CN | 113425304 A | 9/2021 |
| CN | 105615994 B | 10/2021 |
| CN | 109963610 B | 11/2021 |
| CN | 108289709 B | 3/2022 |
| CN | 111246907 B | 7/2022 |
| CN | 107773300 B | 8/2022 |
| CN | 108567424 B | 8/2022 |
| CN | 106859638 B | 10/2022 |
| CN | 108283520 B | 10/2022 |
| CN | 110547865 B | 10/2022 |
| CN | 107343816 B | 11/2022 |
| CN | 115281680 A | 11/2022 |
| CN | 115444549 A | 12/2022 |
| CN | 107343784 B | 2/2023 |
| CN | 110520067 B | 5/2023 |
| CN | 111225627 B | 5/2023 |
| CN | 116158839 A | 5/2023 |
| CN | 106419897 B | 6/2023 |
| CN | 111065350 B | 6/2023 |
| CN | 109259854 B | 10/2023 |
| CN | 111657866 B | 10/2023 |
| CN | 111836579 B | 3/2024 |
| CN | 112704546 B | 3/2024 |
| EP | 0889744 B1 | 1/2004 |
| EP | 1254641 B1 | 11/2008 |
| EP | 1690564 B1 | 4/2009 |
| EP | 1723981 B1 | 8/2010 |
| EP | 2135634 B1 | 10/2011 |
| EP | 2018203 B1 | 6/2012 |
| EP | 1814450 B1 | 1/2013 |
| EP | 2269532 B1 | 3/2013 |
| EP | 2664295 A1 | 11/2013 |
| EP | 2604306 B1 | 1/2014 |
| EP | 2732843 B1 | 5/2014 |
| EP | 2747680 A2 | 7/2014 |
| EP | 2752153 A1 | 7/2014 |
| EP | 2907462 A1 | 8/2015 |
| EP | 2915555 A1 | 9/2015 |
| EP | 1968679 B1 | 9/2016 |
| EP | 2241279 B1 | 9/2016 |
| EP | 2796103 B1 | 2/2017 |
| EP | 3222209 A1 | 9/2017 |
| EP | 2792322 B1 | 10/2017 |
| EP | 2792323 B1 | 10/2017 |
| EP | 3115076 A4 | 10/2017 |
| EP | 3117863 A4 | 10/2017 |
| EP | 3030182 B1 | 1/2018 |
| EP | 3287092 A1 | 2/2018 |
| EP | 3111871 B1 | 3/2018 |
| EP | 3111872 B1 | 4/2018 |
| EP | 3057488 B1 | 5/2018 |
| EP | 2848226 B1 | 7/2018 |
| EP | 3345540 A1 | 7/2018 |
| EP | 3363397 A1 | 8/2018 |
| EP | 2907462 B1 | 9/2018 |
| EP | 3391928 A1 | 10/2018 |
| EP | 3122276 B1 | 11/2018 |
| EP | 3398549 A1 | 11/2018 |
| EP | 3403571 A1 | 11/2018 |
| EP | 1759668 B1 | 12/2018 |
| EP | 3037122 B1 | 12/2018 |
| EP | 2234537 B1 | 1/2019 |

(56) References Cited

FOREIGN PATENT DOCUMENTS

| | | |
|---|---|---|
| EP | 2569040 B1 | 2/2019 |
| EP | 3023052 B1 | 3/2019 |
| EP | 3073908 B1 | 4/2019 |
| EP | 3466363 A1 | 4/2019 |
| EP | 2550989 B1 | 6/2019 |
| EP | 3512589 A1 | 7/2019 |
| EP | 3512590 A1 | 7/2019 |
| EP | 3527125 A1 | 8/2019 |
| EP | 3531903 A1 | 9/2019 |
| EP | 3434218 B1 | 2/2020 |
| EP | 2908723 B1 | 3/2020 |
| EP | 3335658 B1 | 4/2020 |
| EP | 3073907 B1 | 6/2020 |
| EP | 3114987 A1 | 8/2020 |
| EP | 3178516 B1 | 9/2020 |
| EP | 3708104 A1 | 9/2020 |
| EP | 3711662 A1 | 9/2020 |
| EP | 3721796 A1 | 10/2020 |
| EP | 3738508 A1 | 11/2020 |
| EP | 3738509 A1 | 11/2020 |
| EP | 3340916 B1 | 12/2020 |
| EP | 3579908 B1 | 12/2020 |
| EP | 3749174 A1 | 12/2020 |
| EP | 3749192 A1 | 12/2020 |
| EP | 3749195 A1 | 12/2020 |
| EP | 3750475 A1 | 12/2020 |
| EP | 2155301 B1 | 4/2021 |
| EP | 3432820 B1 | 4/2021 |
| EP | 3476331 B1 | 5/2021 |
| EP | 3579758 B1 | 5/2021 |
| EP | 2809254 B1 | 6/2021 |
| EP | 3508245 B1 | 7/2021 |
| EP | 3858277 A1 | 8/2021 |
| EP | 3892221 A1 | 10/2021 |
| EP | 3932343 A4 | 1/2022 |
| EP | 3791820 B9 | 4/2022 |
| EP | 4000506 A1 | 5/2022 |
| EP | 3153124 B1 | 7/2022 |
| EP | 4039215 A1 | 8/2022 |
| EP | 3363397 B1 | 9/2022 |
| EP | 3609414 B1 | 11/2022 |
| EP | 4101372 A1 | 12/2022 |
| EP | 2844193 B1 | 1/2023 |
| EP | 3100696 B1 | 1/2023 |
| EP | 3166524 B1 | 1/2023 |
| EP | 4115936 A1 | 1/2023 |
| EP | 4134032 A1 | 2/2023 |
| EP | 3115076 B1 | 3/2023 |
| EP | 3658054 B1 | 3/2023 |
| EP | 4179991 A1 | 5/2023 |
| EP | 2803329 B1 | 6/2023 |
| EP | 3015064 B1 | 6/2023 |
| EP | 3141183 B1 | 6/2023 |
| EP | 3398549 B1 | 6/2023 |
| EP | 4190232 A1 | 6/2023 |
| EP | 2816966 B1 | 10/2023 |
| EP | 3113671 B1 | 10/2023 |
| EP | 3681427 B1 | 10/2023 |
| EP | 3738509 B1 | 10/2023 |
| EP | 3749195 B1 | 10/2023 |
| EP | 3209234 B1 | 11/2023 |
| EP | 3527125 B1 | 11/2023 |
| EP | 3721796 B1 | 11/2023 |
| EP | 3731747 B1 | 11/2023 |
| EP | 4233699 A3 | 11/2023 |
| EP | 4272631 A2 | 11/2023 |
| EP | 3192442 B1 | 1/2024 |
| EP | 3892221 B1 | 1/2024 |
| EP | 4298995 A2 | 1/2024 |
| EP | 3738508 B1 | 2/2024 |
| IL | 246415 A | 12/2019 |
| IN | 201614021431 A | 12/2016 |
| IN | 201614021432 A | 12/2016 |
| IN | 201614021450 A | 12/2016 |
| JP | 4545384 B2 | 7/2010 |
| JP | 4887810 B2 | 2/2012 |
| JP | 4940332 B2 | 3/2012 |
| JP | 2012055602 A | 3/2012 |
| JP | 2012200509 A | 10/2012 |
| JP | 5154031 B2 | 2/2013 |
| JP | 5193190 B2 | 5/2013 |
| JP | 5372314 B2 | 12/2013 |
| JP | 2014014713 A | 1/2014 |
| JP | 5550150 B2 | 5/2014 |
| JP | 5762697 B2 | 6/2015 |
| JP | 5856712 B2 | 2/2016 |
| JP | 5908270 B2 | 4/2016 |
| JP | 5944331 B2 | 7/2016 |
| JP | 6050522 B2 | 12/2016 |
| JP | 6059737 B2 | 12/2016 |
| JP | 2017012750 A | 1/2017 |
| JP | 2017012755 A | 1/2017 |
| JP | 2017038919 A | 2/2017 |
| JP | 2017051211 A | 3/2017 |
| JP | 2017104552 A | 6/2017 |
| JP | 6246742 B2 | 12/2017 |
| JP | 6342524 B2 | 6/2018 |
| JP | 6434495 B2 | 12/2018 |
| JP | 6445509 B2 | 12/2018 |
| JP | 6445742 B1 | 12/2018 |
| JP | 6466114 B2 | 2/2019 |
| JP | 6479005 B2 | 2/2019 |
| JP | 6515084 B2 | 4/2019 |
| JP | 6528010 B1 | 5/2019 |
| JP | 6655655 B2 | 2/2020 |
| JP | 6746734 B2 | 8/2020 |
| JP | 6776021 B2 | 10/2020 |
| JP | 6776025 B2 | 10/2020 |
| JP | 6786275 B2 | 11/2020 |
| JP | 6821812 B2 | 1/2021 |
| JP | 2021007772 A | 1/2021 |
| JP | 2021501011 A | 1/2021 |
| JP | 6843502 B2 | 3/2021 |
| JP | 6894004 B2 | 6/2021 |
| JP | 6920312 B2 | 8/2021 |
| JP | 6926306 B2 | 8/2021 |
| JP | 6932484 B2 | 8/2021 |
| JP | 6936872 B2 | 9/2021 |
| JP | 2021523755 A | 9/2021 |
| JP | 6980386 B2 | 11/2021 |
| JP | 2022020838 A | 2/2022 |
| JP | 7101228 B2 | 7/2022 |
| JP | 7102558 B2 | 7/2022 |
| JP | 7106301 B2 | 7/2022 |
| JP | 2023002720 A | 1/2023 |
| JP | 7220242 B2 | 2/2023 |
| JP | 7230168 B2 | 2/2023 |
| JP | 7242665 B2 | 3/2023 |
| JP | 7242816 B2 | 3/2023 |
| JP | 7246319 B2 | 3/2023 |
| JP | 2023027202 A | 3/2023 |
| JP | 2023033335 A | 3/2023 |
| JP | 7262919 B2 | 4/2023 |
| JP | 7275333 B2 | 5/2023 |
| JP | 7282759 B2 | 5/2023 |
| JP | 7292822 B2 | 6/2023 |
| JP | 7394766 B2 | 11/2023 |
| JP | 7400050 B2 | 12/2023 |
| JP | 7423550 B2 | 1/2024 |
| JP | 2024012693 A | 1/2024 |
| RU | 2016124794 A | 12/2017 |
| RU | 2016124801 A | 12/2017 |
| RU | 2016125763 A | 1/2018 |
| WO | 9843530 A1 | 10/1998 |
| WO | 0168178 A1 | 9/2001 |
| WO | 2008091197 A1 | 7/2008 |
| WO | 2014113612 A1 | 7/2014 |
| WO | 2015057521 A1 | 4/2015 |
| WO | 2015095577 A1 | 6/2015 |
| WO | 2015130824 A1 | 9/2015 |
| WO | 2016001015 A1 | 1/2016 |
| WO | 2017098198 A1 | 6/2017 |
| WO | 2018005511 A1 | 1/2018 |
| WO | 2018053148 A1 | 3/2018 |

(56) References Cited

FOREIGN PATENT DOCUMENTS

| | | |
|---|---|---|
| WO | 2018053164 A1 | 3/2018 |
| WO | 2018136741 A1 | 7/2018 |
| WO | 2019195439 A1 | 10/2019 |

OTHER PUBLICATIONS

Haldar et al., Circulation AE 2017 (Circ Arrhythm Electrophysiol. 2017;10:e005018. DOI:10.1161/circep.117.005018) p. 6, "Omnipolar Voltage Amplitude Correlates to Largest Measurable Bipolar Vpp" and Fig. 4.

* cited by examiner

RADIO-FREQUENCY ABLATION AND DIRECT CURRENT ELECTROPORATION CATHETERS

CROSS-REFERENCE TO RELATED APPLICATION

The present application is a continuation of application Ser. No. 16/418,296, filed 21 May 2019, now abandoned, which claims priority to U.S. provisional application No. 62/674,314, filed 21 May 2018, which are hereby incorporated by reference as though fully set forth herein.

BACKGROUND a. Field

The instant disclosure relates to radio-frequency ablation catheters for treating myocardial tissue within a cardiac muscle, for example. In particular, the instant disclosure relates to basket and planar array catheters including a plurality of electrodes positioned in a high-density array.

b. Background Art

Catheters have been used for cardiac medical procedures for many years. Catheters can be used, for example, to diagnose and treat cardiac arrhythmias, while positioned at a specific location within a body that is otherwise inaccessible without a more invasive procedure.

Conventional ablation catheters may include, for example, a plurality of adjacent ring electrodes encircling the longitudinal axis of a basket catheter, for example. The ring electrodes may be constructed from platinum or some other metal. These ring electrodes are relatively rigid, and may deliver an ablation therapy (e.g., RF ablation energy) to treat symptoms related to, for example, a cardiac arrhythmia.

When conducting an ablation therapy on myocardial tissue, the beating of the heart, especially if erratic or irregular, makes it difficult to keep adequate contact between electrodes and tissue for a sufficient length of time. These problems are exacerbated on contoured, irregular, or trabeculated surfaces. If the contact between the electrodes and the tissue cannot be sufficiently maintained, quality lesions are unlikely to result.

Typically, cardiac ablation therapies are conducted using a focal point ablation catheter. Focal point ablation catheters deliver energy between a single electrode and a ground pad. As electrophysiology mapping becomes more precise, ablation therapies may likewise be more targeted. More targeted ablation therapies will limit unnecessary tissue damage.

Ablation therapies, such as for atrial fibrillation, have extended durations as the clinician must introduce an electrophysiology mapping catheter into the patient's left atrium, confirm the diagnosis, and determine an ablation therapy strategy before removing the electrophysiology mapping catheter. An ablation catheter is then introduced to complete the ablation therapy, followed by reintroduction of the electrophysiology mapping catheter to confirm the efficacy of the therapy. In view of the foregoing, a catheter capable of both electrophysiology mapping and ablation therapy would be desirable to limit the duration of the operation.

The foregoing discussion is intended only to illustrate the present field and should not be taken as a disavowal of claim scope.

BRIEF SUMMARY

Aspects of the present disclosure are directed to flexible catheters for both electrophysiology mapping and ablation using a high-density array of electrodes. These catheters may be used to detect electrophysiological characteristics of tissue in contact with the electrodes, and conduct monopolar and/or bipolar ablations of the tissue. In particular, the instant disclosure relates to both planar and basket-type end effectors coupled to a distal end of a catheter shaft.

Several embodiments of the present disclosure are directed to a planar array catheter including an elongated catheter shaft and a flexible, planar array coupled to a distal end of the catheter shaft. The elongated catheter shaft defines a longitudinal axis. The flexible, planar array conforms to tissue, and includes two or more struts extending substantially parallel with the longitudinal axis. Each of the struts lay in a common plane and have a plurality of electrodes coupled thereto. The plurality of electrodes detect electrophysiological characteristics of tissue in contact with the planar array and selectively ablate the tissue. In more specific embodiments, the plurality of electrodes in the planar array may operate in both monopolar and bipolar configurations for tissue ablation.

Various embodiments of the present disclosure are directed to basket catheters including an elongated catheter shaft with proximal and distal ends, a flexible basket with a plurality of splines, and a plurality of electrodes mounted to the spline. The flexible basket coupled to the distal end of the catheter shaft and conforming to tissue. The plurality of electrodes detect electrophysiological characteristics of tissue in contact with the basket and selectively ablate the tissue. In some specific embodiments, the basket catheter further includes a plurality of temperature sensors, and ablation controller circuitry. Each of the temperature sensors are mechanically coupled to the splines and placed in thermal communication with at least one of the electrodes. The ablation controller circuitry is communicatively coupled to the plurality of temperature sensors and the plurality of electrodes. The ablation controller circuitry controls the power delivery to each electrode based at least in part upon the temperature measured in proximity to each electrode by the temperature sensors.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings, in which.

Figure 1:
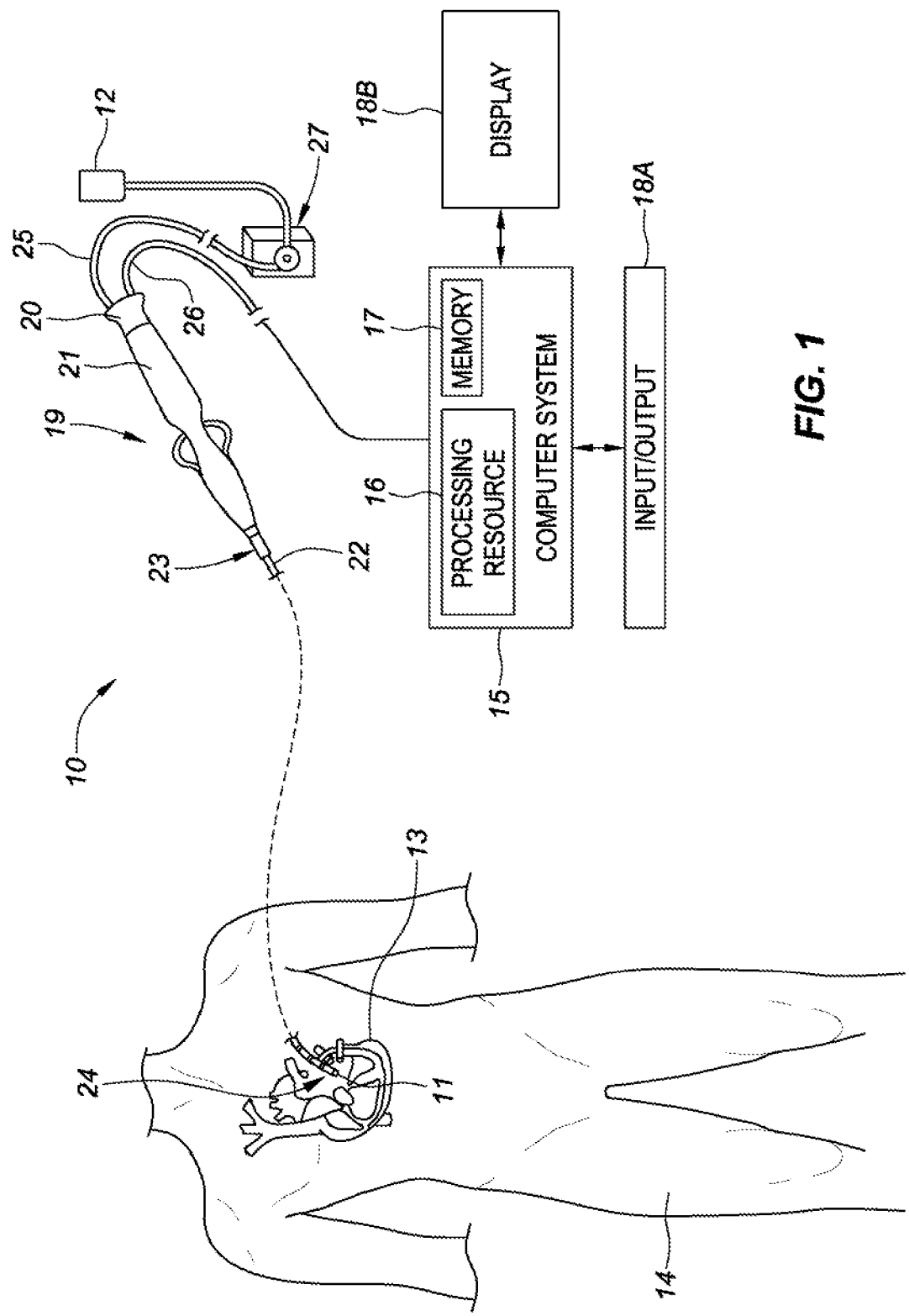
FIG. 1 is a diagrammatic overview of an electrophysiology catheter system, consistent with various embodiments of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

Aspects of the present disclosure are directed to flexible catheters for both electrophysiology mapping and ablation using a high-density array of electrodes. These catheters may be used to detect electrophysiological characteristics of tissue in contact with the electrodes, and conduct monopolar and/or bipolar ablations of the tissue. In particular, the instant disclosure relates to both planar and basket-type end effectors coupled to a distal end of a catheter shaft.

To conduct an electrophysiology mapping of a cardiac muscle, pacing is conducted. During the pacing procedure, adjacent electrodes are assigned to bipole pairings, and each bipole pair samples the electrical characteristics of the tissue between the pair. The resulting electrical signals are received and processed by controller circuitry. The controller circuitry develops an electrophysiology mapping by associating the signal samples from each bipole pair with a location of the tissue sampled by the bipole pair. The electrogram from each bipole pair may be analyzed and various electrical characteristics may be visually indicated on an electrophysiology map by color-coding (or other visual indication scheme, e.g., shading, patterning, etc.). In some embodiments, the color-coding may be based on the electrogram voltage at each location (e.g., mean, average, max, etc.). In other embodiments, the number of times the electrical signal exceeds a threshold voltage (or a voltage slope changes signs) during a sampling window may be visually displayed on the map. In yet other embodiments, total energy sampled during a time window may be displayed. Various other methods of fractionation accounting are known, and may be used as one or more factors of the resulting color-code displayed on the electrophysiology map. These electrophysiology maps may be used by a clinician to verify a diagnosis, provide insight into a desired ablation therapy strategy, and to verify the efficacy of the therapy.

Aspects of the present disclosure are directed to intravascular catheters with end effectors capable of electrophysiology mapping and mono/bipolar radio-frequency ablation treatment. Historically, cardiac ablation therapy has been conducted using point-by-point ablation techniques, delivering energy between a single electrode positioned on the distal tip of the catheter and a ground pad electrically coupled to the patient's chest. However, high-density electrophysiology mapping catheters have facilitated improved diagnostic specificity, and thereby a clinician may use the electrophysiology maps to more precisely target an ablation therapy to problematic tissue (e.g., such as tissue containing arrhythmic foci). This is particularly desirable as a clinician wishes to minimize the ablation of healthy myocardial tissue as much as possible, to maintain healthy functionality of the left atrium. To further improve ablation therapy workflow, aspects of the present disclosure are directed to using a single catheter to conduct both the electrophysiology mapping of the left atrium, as well as the ablation therapy. By combining such functionality into a single catheter, length of an ablation therapy (and operating room time) may be reduced. More specific embodiments of the present disclosure are directed to controlling ablation depth of an ablation catheter. Such embodiments are facilitated by improved three-dimensional electrophysiology mapping, which indicate the electrophysiology characteristics of the contacted myocardial tissue sub-surface. The ablation therapy may then be customized to provide depth-varying tissue ablation therapy throughout the left atrium using a combination of monopolar and bipolar type radio-frequency tissue ablation.

In many adults, myocardial tissue depth is typically less than 3 millimeters, and often less than 2 millimeters. Aspects of the present disclosure are directed to customizing a patient's tissue ablation therapy, to alleviate symptoms related to a cardiac arrhythmia for example, by varying ablation therapy treatment depths and to only treat compromised tissue. For example, an ablation therapy treatment plan may use a combination of monopolar RF (ablating between a single electrode and a ground pad) and bipolar RF modes (ablating between electrodes on the catheter) to vary an ablation treatment depth. Such variable-depth ablation therapy treatment mitigates risk to susceptible tissue such as the phrenic nerve. In more specific embodiments, multiplexing or selected sequential energy delivery for lesion formation may be utilized to further customize the ablation therapy.

In some specific aspects of the present disclosure, a basket catheter including 8 splines is disclosed. Each of the splines is comprised of a shape memory material which returns to a semi-circular shape upon exiting an introducer. Each of the splines is equally distributed circumferentially about the basket relative to the other splines. When expanded, the 8 splines form a substantially circular-shaped basket. Each of the splines includes a row of electrodes extending along a length of the splines. The electrodes may be evenly distributed along the length of the splines, or unevenly distributed along the length of the splines for specialized applications. For example, the distribution of the electrodes may be weighted toward a distal end of the basket where the basket catheter is intended, for example, to diagnose cardiac arrhythmias. Many cardiac arrhythmias are triggered by stray electrical signals emanating from one or more of the pulmonary veins. Assuming a transseptal approach to the left atrium, the distal end of the basket, including its high-density array of electrodes, would be orientated by a clinician with the pulmonary veins. Once in place within the left atrium, the basket catheter is capable of conducting an electrophysiology mapping of the left atrium, ablating myocardial tissue in proximity to the pulmonary veins to alleviate symptoms related to atrial fibrillation, and re-mapping the left atrium to verify the efficacy of the therapy.

In some specific aspects of the present disclosure, a planar array catheter including five struts is disclosed. Each of the struts may be aligned with, and extend parallel to, a longitudinal axis of the catheter shaft. Each strut is coupled to the other struts of the planar array at proximal and distal ends. The struts each include a row of electrodes extending along a length of the struts. In some specific embodiments, the electrodes are evenly distributed along the length of the struts and between adjacent struts of the planar array. According to various embodiments, the planar catheter array of the present disclosure may include at least four struts, five struts, six struts, seven struts, or perhaps even eight struts. In the embodiment illustrated in FIG. 3A, the array contains five struts.

The electrodes disclosed herein may be ring electrodes, and/or printed (spot) electrodes on substrates (e.g., flexible circuit boards). Advantageously, printed electrodes may be spaced more closely than ring electrodes. In some embodiments, for example, printed electrodes spaced 0.1 mm apart have been successfully deployed in a planar array catheter. More typically, ring electrodes and printed electrodes have been advantageously spaced 0.5 mm to 4 mm apart. It has been found that such electrode spacing facilitates desirable electrophysiology mapping granularity in a number of cardiovascular applications, for example. Moreover, high-density positioning of electrodes about a planar array or basket catheter may facilitate customizable ablation therapies which minimize the amount of lesioned tissue necessary to alleviate the effects of cardiac arrhythmias, such as atrial fibrillation, on a patient.

Conventional mapping catheter designs employ bipole electrode configurations to detect, measure, and display electrical signals from the heart, and point-by-point ablation catheters with monopole electrode configurations to facilitate tissue ablation. However, various aspects of the present disclosure are directed to using a combination of monopolar and bipolar configurations on the catheter to facilitate treatment of, for example, atrial fibrillation. The relative selection of monopole or bipole ablation treatment at a given tissue location may be based, for example, on the desired ablation depth or width. In some specific embodiments, ablation controller circuitry may receive an electrophysiology map of a target tissue area and determine the type of ablation therapy each tissue region within a target tissue area will receive. Alternatively, a clinician may manually design the ablation therapy based on an electrophysiology map provided, or otherwise approve/modify the treatment strategy designed by the ablation controller circuitry.

A basket catheter for ablation therapy, consistent with the present disclosure, may include a plurality of electrodes distributed about one or more of the splines which form the basket. Each of the electrodes may operate in a monopole or bipole configuration, or in both configurations simultaneously. That is, a single electrode may transmit radio-frequency energy to an adjacent electrode on the basket catheter and a patch electrode on a patient's chest simultaneously. In some more specific embodiments, a thermocouple may be placed beneath (or otherwise in close proximity to) one or more of the electrodes to enable temperature controlled radio-frequency tissue ablation.

Details of the various embodiments of the present disclosure are described below with specific reference to the figures.

FIG. 1 is a diagrammatic overview of an electrophysiology catheter system, consistent with various embodiments of the present disclosure.

Referring now to the drawings wherein like reference numerals are used to identify identical components in the various views, FIG. 1 generally illustrates an electrophysiology catheter system 10 for force detecting having an elongated medical device 19 that includes a sensor assembly 11 (e.g., a plurality of electrodes for electrophysiology mapping and ablation) configured to be used in the body for medical procedures. The elongated medical device 19 may be used for diagnosis, visualization, and/or treatment of tissue 13 (such as cardiac or other tissue) in the body. For example, the medical device 19 may be used for ablation therapy of tissue 13 or mapping purposes in a patient's body 14. FIG. 1 further shows various sub-systems included in the overall system 10. The system 10 may include a main computer system 15 (including an electronic control unit 16 and data storage 17, e.g., memory). The computer system 15 may further include conventional interface components, such as various user input/output mechanisms 18A and a display 18B, among other components. Information provided by the sensor assembly 11 may be processed by the computer system 15 and may provide data to the clinician via the input/output mechanisms 18A and/or the display 18B, or in other ways as described herein.

In the illustrative embodiment of FIG. 1, the elongated medical device 19 may include a cable connector or interface 20, a handle 21, a tubular body or shaft 22 having a proximal end 23 and a distal end 24. The elongated medical device 19 may also include other conventional components not illustrated herein, such as a temperature sensor, additional electrodes, and corresponding conductors or leads. The connector 20 may provide mechanical, fluid and/or electrical connections for cables 25, 26 extending from a fluid reservoir 12 and a pump 27 and the computer system 15, respectively. The connector 20 may comprise conventional components known in the art and, as shown, may be disposed at the proximal end of the elongated medical device 19.

The handle 21 provides a portion for a user to grasp or hold the elongated medical device 19 and may further provide a mechanism for steering or guiding the shaft 22 within the patient's body 14. For example, the handle 21 may include a mechanism configured to change the tension on a pull-wire extending through the elongated medical device 19 to the distal end 24 of the shaft 22 or some other mechanism to steer the shaft 22. The handle 21 may be conventional in the art, and it will be understood that the configuration of the handle 21 may vary.

The computer system 15 may utilize software, hardware, firmware, and/or logic to perform a number of functions described herein. The computer system 15 may be a combination of hardware and instructions to share information. The hardware, for example may include processing resource 16 and/or a memory 17 (e.g., non-transitory computer-readable medium (CRM) database, etc.). A processing resource 16, as used herein, may include a number of processors capable of executing instructions stored by the memory resource 17. Processing resource 16 may be integrated in a single device or distributed across multiple devices. The instructions (e.g., computer-readable instructions (CRI)) may include instructions stored on the memory 17 and executable by the processing resource 16 for force detection.

The memory resource 17 is communicatively coupled with the processing resource 16. A memory 17, as used herein, may include a number of memory components capable of storing instructions that are executed by processing resource 16. Such a memory 17 may be a non-transitory computer readable storage medium, for example. The memory 17 may be integrated in a single device or distributed across multiple devices. Further, the memory 17 may be fully or partially integrated in the same device as the processing resource 16 or it may be separate but accessible to that device and the processing resource 16. Thus, it is noted that the computer system 15 may be implemented on a user device and/or a collection of user devices, on a mobile device and/or a collection of mobile devices, and/or on a combination of the user devices and the mobile devices.

The memory 17 may be communicatively coupled with the processing resource 16 via a communication link (e.g., path). The communication link may be local or remote to a computing device associated with the processing resource 16. Examples of a local communication link may include an electronic bus internal to a computing device where the memory 17 is one of a volatile, non-volatile, fixed, and/or removable storage medium in communication with the processing resource 16 via the electronic bus.

Figure 2A:
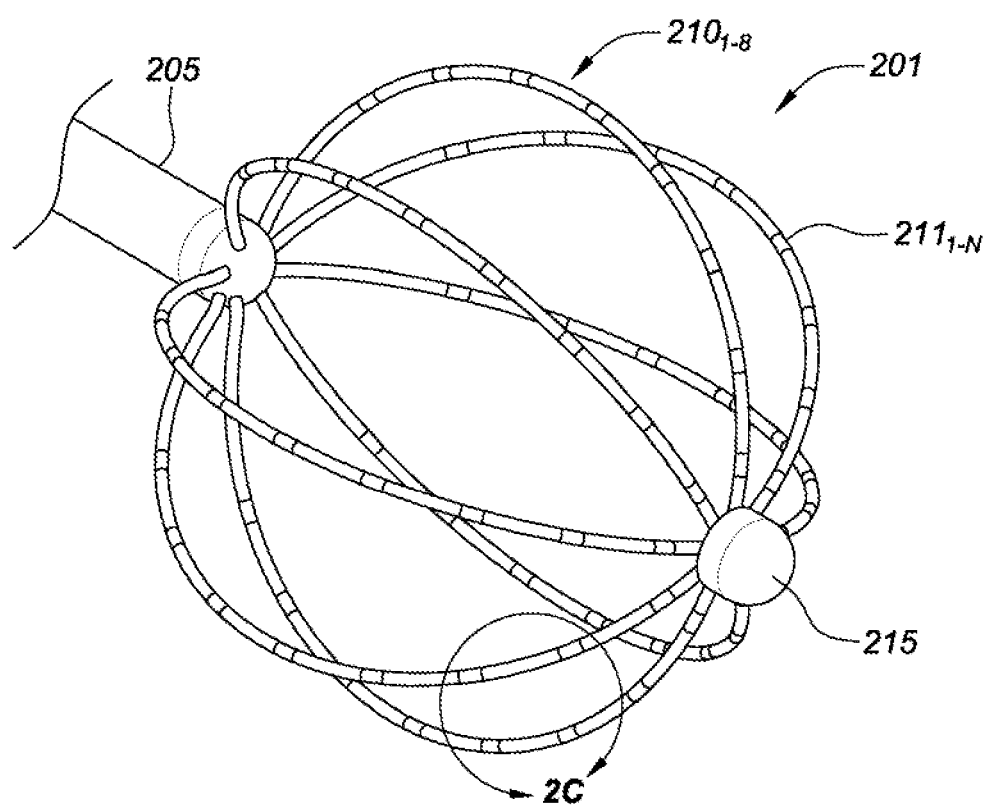
FIG. 2A is an isometric side view of a basket end effector of an electrophysiology catheter, consistent with various embodiments of the present disclosure.

FIG. 2A is an isometric side view of a basket end effector (also referred to as a basket catheter) of an electrophysiology catheter, consistent with various embodiments of the present disclosure. The basket catheter 201 of FIG. 2A is shown in an expanded configuration. The basket 201 is comprised of a plurality of splines $210_{1-8}$ which are coupled to a catheter shaft 205 at a proximal end and to a distal cap 215 (or one another) at a distal end. While the present embodiment presents a basket comprised of eight splines $210_{1-8}$, basket catheters with three or more splines are readily envisioned, with the design depending on an intended clinical application and desired electrophysiology mapping granularity. To facilitate expansion/contraction of the basket, the splines $210_{1-8}$ may be comprised of a shape-memory alloy (e.g., nitinol) which returns to a semi-circular shape after exiting an introducer. In yet other embodiments, the basket catheter may utilize a deployment member to expand/contract the basket.

Figure 2B:
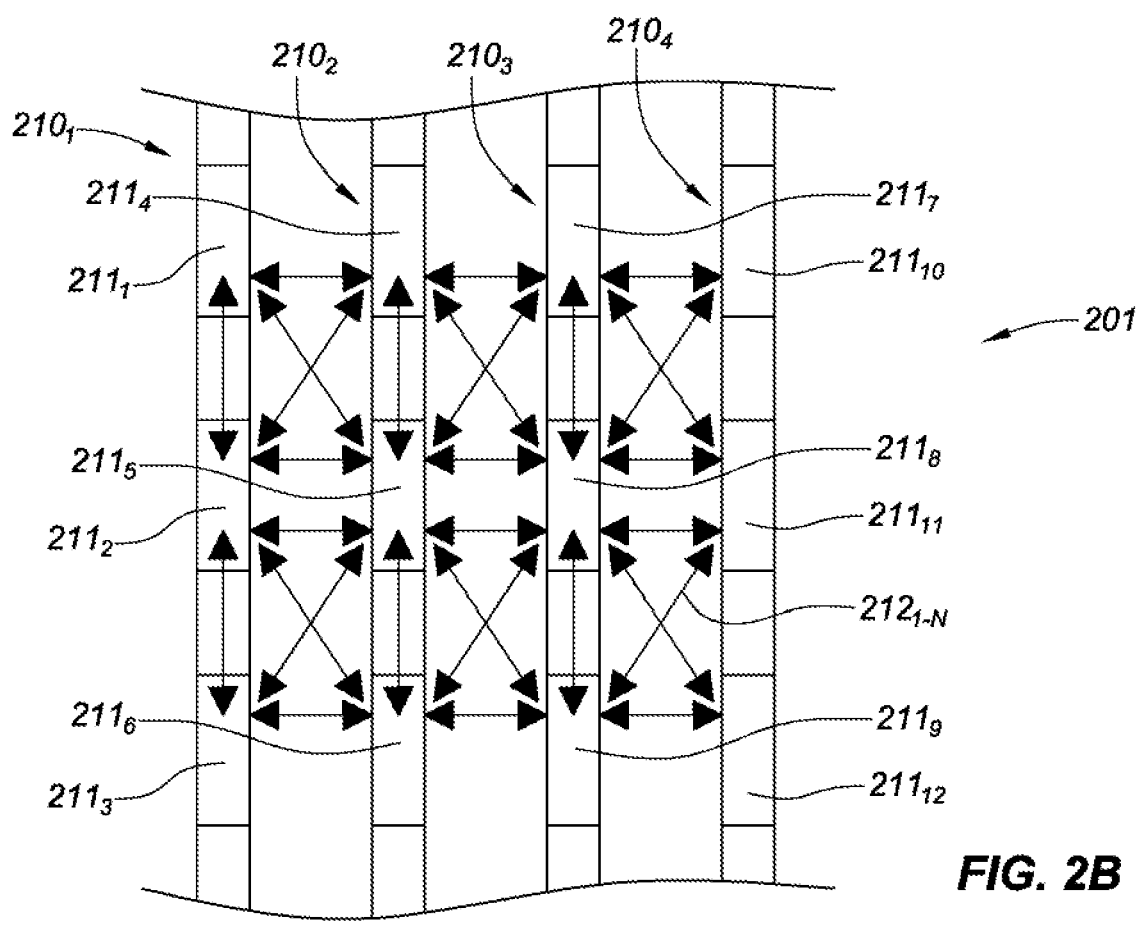
FIG. 2B is a close-up view of a portion of four adjacent splines of the basket end effector of FIG. 2A, consistent with various embodiments of the present disclosure.
Figure 2C:
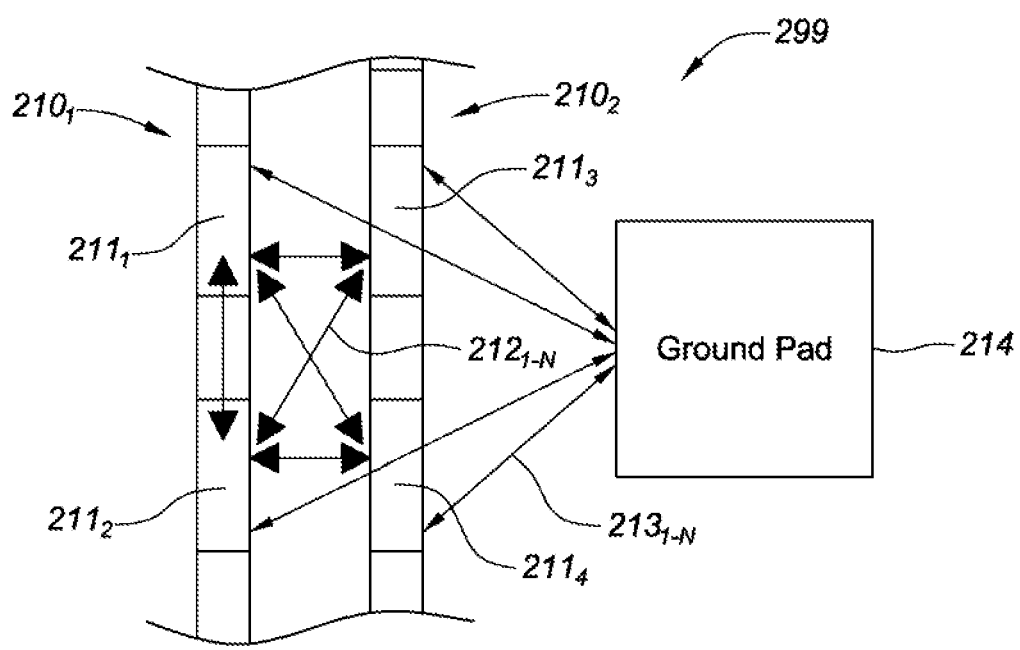
FIG. 2C is a close-up view of a portion of two adjacent splines of the basket end effector of FIG. 2A and a ground pad which together form a radio-frequency ablation system, consistent with various embodiments of the present disclosure.

In the present embodiment, each of the splines $210_{1-8}$ includes a plurality of electrodes $211_{1-N}$ distributed about a length of each spline. While the embodiment presented in FIGS. 2A-C depicts electrode $211_{1-N}$ regularly distributed along the length of each spline, other embodiments may include unevenly distributed electrodes along the splines. For example, in pulmonary vein electrophysiology mapping applications, only a distal portion of the basket may be in contact with tissue proximal the pulmonary veins. Accordingly, a distribution of electrodes $211_{1-N}$ may be weighted toward a distal end of the basket 201 to facilitate enhanced electrophysiology mapping granularity in proximity to the pulmonary veins.

The electrodes $211_{1-N}$ may be used in various bipole configurations to facilitate measurement of electrical characteristics of tissue in contact with the electrodes. A first bipole pair may include a pair of electrodes 211 along a length of a spline 210, facilitating the collection of tissue electrical characteristic data in an orientation substantially parallel with the catheter's longitudinal axis. A second, orthogonal bipole pair may extend laterally across adjacent splines 210, facilitating the collection of tissue electrical characteristic data in an orientation substantially transverse to the catheter's longitudinal axis. To facilitate collecting this electrical data, these bipole electrode pairs may be independently addressable by signal processing circuitry. The signal processing circuitry analyzes the received signals from the various bipole electrode pairs to assemble a electrophysiology map which visualizes the electrophysiology data sensed by the basket catheter of the tissue in contact with the electrodes.

In various embodiments consistent with the present disclosure, splines 210 may be formed from flexible electronic circuit boards with each of the electrodes 211 coupled thereto and communicatively coupled to signal processing circuitry via electrical traces that extend along interior or exterior layers of the flexible printed circuit board. In some specific embodiments, each of the splines 210 may consist of nitinol. In such embodiments, the flex circuit may be either bonded directly to the nitinol, or, alternatively, the flex circuit may be directly bonded to Pebax™ tubing which houses the nitinol spline internally.

In some embodiments, the electrodes 211 may be 0.8 millimeters in diameter with a total surface area of 0.5 mm². The electrodes 211 on the basket catheter 201 need not be uniform in size and shape. For example, embodiments consistent with the present disclosure may include electrodes capable of electrophysiology mapping, RF tissue ablation, and optionally facilitating localization in an impedance or hybrid-based catheter navigation system (e.g., MediGuide™ System, and/or EnSite™ NavX™ System, each from Abbott).

While it may be desirable in some embodiments to have equal spacing between all of the electrodes 211 both on a spline 210 and between splines, knowledge of the relative spacing between each of the electrodes which form bipole pairs is sufficient to accurately capture electrical characteristic data of tissue in contact with the electrodes. In some specific embodiments, an edge-to-edge spacing for one or more of the bipole pairs of electrodes may be between 2-2.5 millimeters. In yet other specific embodiments, center-to-center spacing of the electrodes in a bipole pair may be between 0.5-4 millimeters.

In some specific embodiments, some of electrodes 211 on basket 201 may be multi-purpose, while other electrodes are single-purpose. For example, some of the electrodes may function as both navigation, ablation, and electrophysiology mapping electrodes, others may function only as electrophysiology mapping electrodes, and yet other electrodes may function only as navigation electrodes.

As further shown in FIG. 2A, a distal cap 215 may serve several purposes including coupling distal ends of the splines $210_{1-8}$ back to one another (near a longitudinal axis of the catheter), and providing a distal most surface of the catheter that prevents unintentional trauma to tissue contacted therewith.

In various embodiment consistent with the present disclosure, each spline of the basket catheter may be coupled to one or more steering wires which when actuated expand and/or contract the splines to form the desired shape.

While the present disclosure is directed toward a basket catheter 201 with eight electrodes 211 on each spline 210, various other implementations are readily envisioned. For example, the basket catheter may include more or less splines and/or more or less electrodes on each respective spline.

As discussed in more detail below, one particular advantage of a basket catheter capable of both electrophysiology mapping and ablation therapy is reduction in surgery time as the clinician need not swap out the electrophysiology mapping catheter with an ablation catheter after confirming a treatment strategy. Moreover, the need for magnetic and/or impedance-based localization of the ablation catheter within the patient's cardiac muscle may be reduced as the relative location of target tissue for ablation is already known by virtue of the electrophysiology mapping and the static position of the basket catheter within the patient's left atrium.

FIG. 2B is a close-up view of a portion of four adjacent splines $210_{1-4}$ of the basket 201 of FIG. 2A, consistent with various embodiments of the present disclosure. Each of the splines 210 include a number of electrodes $211_{1-12}$ which may be used to sense the electrophysiological characteristics of tissue (often operating in a bipolar configuration with another adjacent electrode), and/or ablate tissue in contact therewith. The electrodes may ablate tissue using a bipolar configuration, or a uni-polar configuration where one or more of the electrodes are paired with a ground pad which is coupled to a patient's chest, for example. As shown in FIG. 2B, a number of bipolar electrode pairings $212_{1-N}$ are shown. These pairings may extend along a longitudinal axis of a spline, transverse to the longitudinal axis of the spline, or the electrode pairings may extend diagonally between two adjacent splines. Such a system may conduct electrophysiology mapping using a bipolar configuration of electrodes across a surface of a basket catheter, and/or conduct precise tissue ablation therapies which limit the necrosis of healthy tissue. For example, based on a generated electrophysiology map of tissue in a patient's left atrium, a bipolar ablation therapy may be implemented that ablates only tissue that is susceptible to transmitting stray electrical signals and/or myocardial tissue containing arrhythmic foci (which may generate such electrical signals).

One particular benefit of bipolar ablation therapy is that the actual energy delivered to target tissue is known, due to the close proximity of the positive and negative electrodes. Moreover, bipolar ablation therapy also limits energy delivery to non-target tissue by virtue of the relative proximity of the electrodes.

While FIG. 2B depicts bipole pairs of electrodes which are immediately adjacent to one another, other bipole pair arrangements are readily envisioned. For example, pairs of electrodes that are not immediately adjacent. For example, tissue ablation may be achieved to tissue in proximity to electrodes $211_1$ and $211_{12}$, when the electrodes are operated in a bipolar arrangement. In some embodiments a first number of electrodes (e.g., electrodes $211_{1-3}$) on a first spline $210_1$ may be operated in a bipolar arrangement with a second number of electrodes (e.g., electrodes $211_{4-6}$) on a second spline $210_2$. In yet further embodiments, a first number of electrodes (e.g., electrodes $211_{1-3}$) on a first spline $210_1$ may be operated in a bipolar arrangement with a third number of electrodes (e.g., electrodes $211_{7-9}$) on a third spline $210_3$. Further, a first number of electrodes (e.g., electrodes $211_{1-3}$) on a first spline $210_1$ may be operated in a bipolar arrangement with a fourth number of electrodes (e.g., electrodes $211_{10-12}$) on a fourth spline $210_4$.

FIG. 2C is a close-up view of a portion of two adjacent splines $210_{1-2}$ of the basket catheter 201 of FIG. 2A and a ground pad 214 which together form a radio-frequency ablation system 299. As discussed in FIG. 2B, each spline 210 includes a number of electrodes $211_{1-4}$. Each electrode may be paired with another adjacent electrode to facilitate bipolar electrophysiology mapping and/or tissue ablation (e.g., bipolar electrode pairings $212_{1-N}$). Alternatively, or simultaneously, the electrodes $211_{1-4}$ may also be paired with a ground pad 214 to operate in a monopolar ablation therapy configuration (e.g., monopolar electrode pairings $213_{1-N}$). During an ablation therapy, electrodes operating in a monopolar configuration will achieve greater lesion depth, and bipolar configuration electrodes will create more precisely located lesions.

Figure 3A:
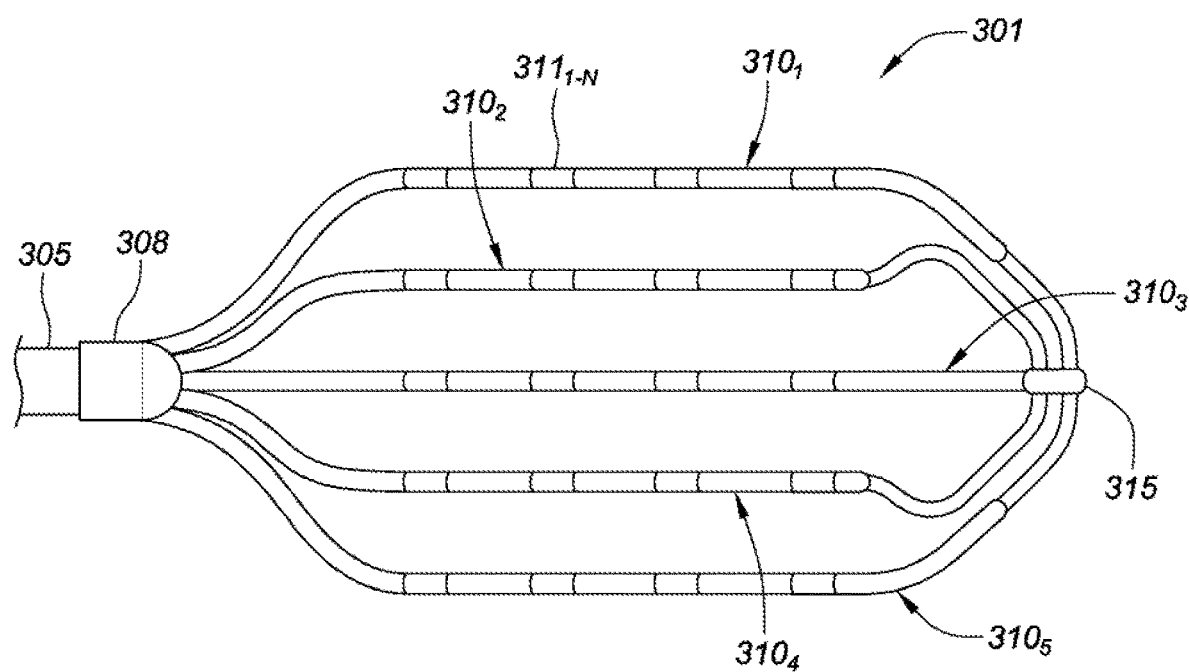
FIG. 3A is a top view of a planar end effector of an electrophysiology mapping catheter, consistent with various embodiments of the present disclosure.

FIG. 3A is a top view of a planar array 301 of an electrophysiology mapping catheter, consistent with various embodiments of the present disclosure. The planar array 301 of the electrophysiology mapping catheter includes a high-density array of electrodes $311_{1-N}$. The planar array 301 forms a flexible array of the electrodes $311_{1-N}$. This array of electrodes is coupled to a flexible framework of struts $310_{1-5}$ which extend along a plane that is substantially parallel with a longitudinal axis of catheter shaft 305. Each of the struts is precisely, laterally separated from each other to facilitate exact spacing between electrodes $311_{1-N}$ on adjacent struts $310_{1-5}$, and the struts are coupled to one another at distal and proximal ends (e.g., at a distal tip 315 and bushing 308).

As shown in FIG. 3A, each of the five struts $310_{1-5}$ may carry a plurality of electrodes 311, with the spacing of the electrodes along a length of the strut being the same (or at least known). Similarly, the spacing between electrodes 311 across struts 310 of the array may also be equal (or at least known). The result is a plurality of electrode bipole pairs with known spacing. For example, in some embodiments the center-to-center electrode spacing of a bipole pair may be between 0.5-4 mm. In yet more specific embodiments, the center-to-center electrode spacing of a bipole pair may be less than 0.5 millimeters (e.g., 0.1 mm). While the present embodiment is directed to bipole pairs with equal center-to-center spacing, various other embodiments of an electrode array consistent with the present disclosure may include an electrode array with equal edge-to-edge spacing. For example, in some embodiments the edge-to-edge electrode spacing may be between 0.5-4 mm. In yet more specific embodiments, the edge-to-edge electrode spacing may be less than 0.5 millimeters (e.g., 0.1 mm). Consideration of edge-to-edge spacing may be desirable where the electrodes 311 of the array 301 have different relative sizes (or surface areas).

Although the planar array 301 in FIG. 3A depicts five struts $310_{1-5}$, the catheter may comprise more or less struts, with spacing between each respective strut based on a desired electrode spacing for a given electrophysiology application. Additionally, while the planar array 301 depicted in FIG. 3A shows 20 electrodes 311, the planar array may include more or fewer than 20 electrodes, and each strut need not have the same number of electrodes as adjacent struts.

In some embodiments, electrodes $311_{1-N}$ may be used in diagnostic, therapeutic, and/or mapping procedures. For example and without limitation, the electrodes 311 may be used for electrophysiological studies, pacing, cardiac mapping, and ablation. In some embodiments, the electrodes 311 may perform unipolar and/or bipolar tissue ablation therapy. The ablation therapy may create specific lines or patterns of lesions. In some embodiments, the electrodes 311 may receive electrical signals from a pacing electrode, which can be used for electrophysiological studies/mapping. Importantly, as the electrode spacing between adjacent electrodes on a strut 310, and those on adjacent struts, are the same (or otherwise known), bipole pairs with varying relative orientations may be sampled to determine electrical characteristics of the tissue in contact with the bipole pairs. In some embodiments, the electrodes 311 may perform a location or position sensing function related to localization (e.g., determine location and/or orientation of the catheter 301).

The planar array 301 is coupled to a distal end of a catheter shaft 305 at a bushing 308 (also referred to as a connector). The catheter shaft 305 may also define a catheter shaft longitudinal axis. In the present embodiment, each of the struts $310_{1-5}$ extend parallel to the longitudinal axis. The catheter shaft 305 may be made of a flexible material, such that it can be threaded through a tortuous vasculature of a patient. In some embodiments, the catheter shaft 305 can include one or more ring electrodes disposed along a length of the catheter shaft. The ring electrodes may be used for diagnostic, therapeutic, localization and/or mapping procedures, for example. In one embodiment, planar array 301 may include one or more magnetic field sensors configured for use with an electromagnetic localization system such as the MediGuide™ System sold by St. Jude Medical, Inc. of St. Paul, Minnesota.

The planar array 301 may be adapted to conform to tissue (e.g., cardiac tissue). For example, when the planar array contacts tissue, each strut $310_{1-5}$ may independently deflect to conform to the tissue. The ability for the planar array to deflect in response to tissue may be particularly beneficial when the planar array comes into contact with contoured, irregular, or trabeculated tissue. In some embodiments, the struts 310 (or the understructure of the struts) may be constructed from a flexible or spring-like material such as nitinol and/or a flexible substrate. The construction of the planar array struts $310_{1-5}$ (including, for example, the length and/or diameter of the struts, and material) may be tailored to achieve desired resiliency, flexibility, foldability, conformability, and stiffness characteristics. Moreover, in some embodiments it may be desirable to vary one or more characteristics from the proximal end of a strut to the distal end of the strut, or between or among the plurality of struts forming the planar array 301. The collapsibility of materials such as nitinol and/or a flexible substrate provides the added benefit of facilitating insertion of the planar array into a delivery sheath or introducer, whether during delivery of the catheter into the body or removal of the catheter from the body at the end of a procedure.

Planar array catheters, including the high-density electrode array positioned thereon, may be used for, for example: (1) defining regional propagation maps of particularly sized areas on the walls of the heart; (2) identifying complex fractionated atrial electrograms for ablation; (3) identifying localized, focal potentials between the electrodes for higher electrogram resolution; and/or (4) more precisely targeting areas for ablation. Additionally, the catheters described herein may find application in epicardial and/or endocardial use, and more specifically for treating symptoms associated with Brugada syndrome. For example, the planar array embodiments depicted herein may be used in epicardial procedures where the planar array of electrodes is positioned between the myocardial surface and the pericardium. Alternatively, the planar array may be used in an endocardial procedure to sweep and/or analyze the inner surfaces of the myocardium and create high-density maps of the heart tissue's electrical properties.

While various embodiments of the planar array 301 disclosed in the present disclosure are depicted with ring electrodes $311_{1-N}$ coupled to the struts $310_{1-5}$, embodiments with spot-type electrodes coupled to the struts are readily envisioned. Moreover, in yet further embodiments, the struts of the planar array may comprise flexible thin films compatible with printed circuit manufacturing techniques and/or have such thin films coupled to structural elements of the strut (e.g., nitinol-based structural elements). In such embodiments, spot-type electrodes may be printed onto the struts themselves. In flexible printed circuit embodiments of the present disclosure, the printed electrodes may be electrically coupled to signal processing circuitry and/or driver circuitry via traces extending on or within the one or more thin film layers. As many electrophysiology mapping applications require high signal fidelity, it is desirable to limit the transmission length of the analog signal, shield the transmission line itself, and/or convert the analog signal to a digital signal close to the source of the analog signal. Accordingly, aspects of the present disclosure are directed to placing signal processing circuitry (e.g., analog-to-digital converters, signal conditioning such as noise filtration and bandpass filters), and/or driver circuitry on the struts $310_{1-5}$ or in close proximity thereto.

In embodiments of the planar array 301 including ring electrodes $311_{1-N}$, the ring electrodes of the high-density electrode array may include the same type of electrode or a variety of various electrode types. For example, electrodes with smaller surface area may be used exclusively for electrophysiology mapping, while larger surface area electrodes may be used for mapping, tissue ablation, and/or localization. In some specific embodiments, the electrode array may include one or more slightly enlarged ring electrodes. These slightly enlarged electrodes may be used, for example, for more precise localization of the flexible array in mapping and navigation systems. It may also be possible to drive ablation current between these enlarged electrodes, if desired, for bipolar ablation, or, alternatively to drive ablation current in unipolar mode between one or more of these enlarged ring electrodes and, for example, a ground or patch electrode located on a patient (e.g., on the patient's back). Similarly, the electrodes $311_{1-N}$ in some embodiments may all be capable of performing unipolar or bipolar ablation therapies. Alternatively or concurrently, current may travel between one or more of the enlarged electrodes and any one, or all, of the electrodes. This unipolar or bipolar ablation therapy techniques may be used to create specific lesion lines or lesion patterns. As also seen in FIG. 3A, there may be a distal tip 315 where one or more of the struts $310_{1-5}$ come together. This distal tip 315 may be constructed from metal or some other radiopaque material to provide fluoroscopy visualization. The distal tip 315 may further facilitate (semi-) independent planar movement between the struts $310_{1-5}$.

In some embodiments of the present disclosure, the mapping catheter 301 may include steering wires which extend a length of catheter shaft 305. Prior to reaching a bushing 308 that couples the catheter shaft 305 to struts $310_{1-5}$ of planar array 301, the steering wires may be coupled to steering rings which receive a tension from a proximal end of the steering wires and facilitates steering the catheter shaft 305 and the planar array 301 through a patient's vasculature. As further shown in FIG. 3A, each of the struts $310_{1-5}$ includes a plurality of electrodes $311_{1-N}$ distributed along a length of the struts. In the present embodiment, each of the electrodes are equally spaced from each of the adjacent electrodes. When controller circuitry samples electrical signals from bipole pairs of electrodes within the planar array 301, each of the bipole pairs will detect various electrical characteristics indicative of the tissue health in contact with the electrodes. The five struts $310_{1-5}$ are designed to maintain the electrodes $311_{1-N}$ in a spaced relationship so that each bipole pair of electrodes captures electrophysiology data of tissue across a known distance.

While many embodiments of the present disclosure are directed to electrophysiology mapping, embodiments of the present disclosure may also be configured for pacing (as well). For example, one or more electrodes $311_{1-N}$ may send pacing signals to, for example, cardiac tissue.

Though not shown in FIG. 3A, various embodiments of the planar array catheter 301 may include one or more irrigation ports. For example, proximal irrigant port(s) may be located on/at the distal end of proximal bushing 308, the proximal irrigant port(s) positioned to deliver irrigant to or near the point where the electrode carrying struts $310_{1-5}$ exit from the distal end of the proximal bushing that is mounted on the distal end of the catheter shaft 305 in this embodiment. In some more specific embodiments, second, distal irrigation port(s) may be located near the distal intersection of the struts $310_{1-5}$ and on or near distal tip 315. In yet further embodiments, if desired, multiple irrigation ports could be present at various positions along the struts 310. Where more than one irrigant port is positioned at proximal and/or distal ends of the planar array 301, more uniform irrigant distribution at or near the proximal/distal apex of the struts 310 may be facilitated.

Figure 3B:
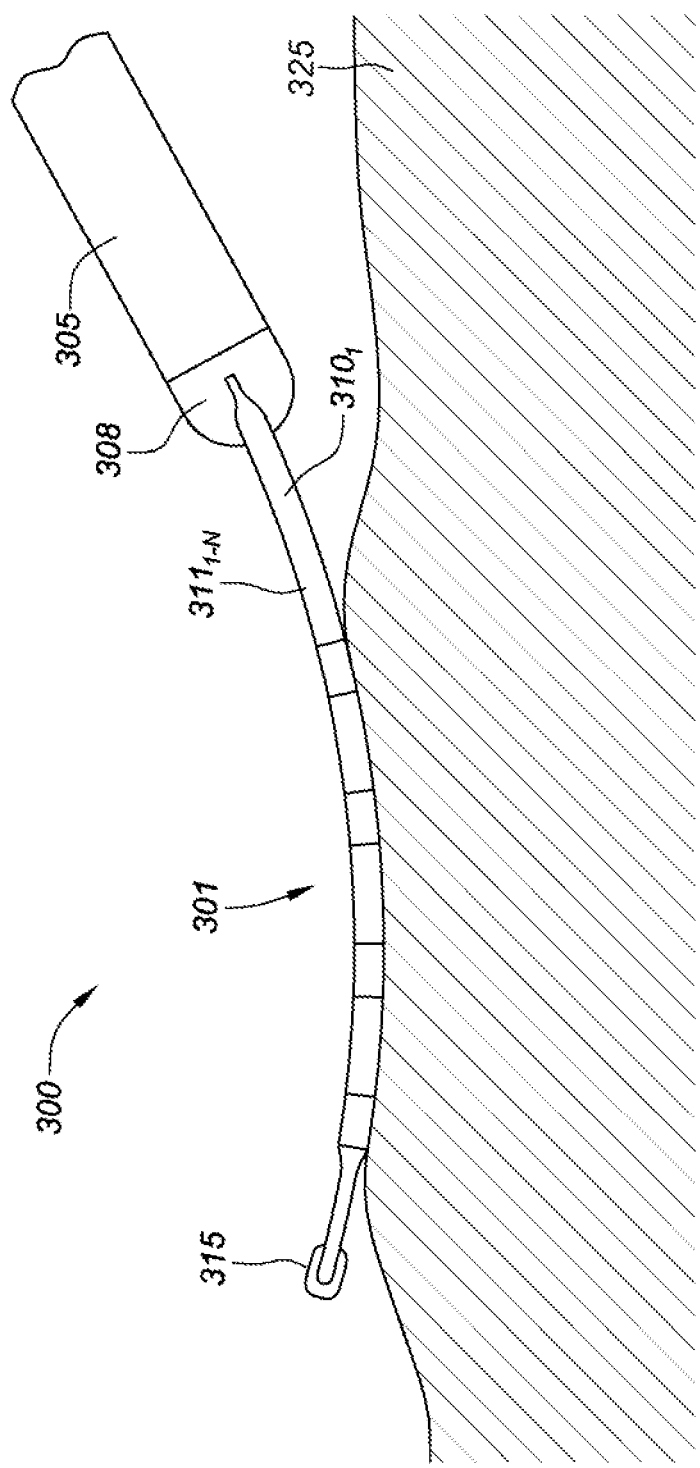
FIG. 3B depicts the planar array catheter of FIG. 3A with an array of electrodes contacting tissue, consistent with various embodiments of the present disclosure.

FIG. 3B depicts the planar array catheter 300 of FIG. 3A with an array 301 of electrodes $311_{1-N}$ contacting tissue 325. The tissue 305 in the present embodiment is depicted as trabeculated, irregular, or contoured tissue. As shown in FIG. 3B, the flexible struts of the planar array, including flexible strut $310_1$, conforms to the tissue 325, enabling a physician to place the planar array 301 (and its electrodes $311_{1-N}$) into constant contact with the tissue 325. Each strut $310_{1-5}$ may independently deflect to conform to the tissue. As a result, the electrical signals (indicative of the tissue's electrical activity) sampled by the planar array exhibit enhanced accuracy, and thereby have improved diagnostic value. Each of the flexible struts include a plurality of electrodes $311_{1-N}$, and are coupled to the other adjacent struts of the planar array 301 at distal member 315 and bushing 308. The bushing 308 further couples the planar array 301 to shaft 305.

Figure 3C:
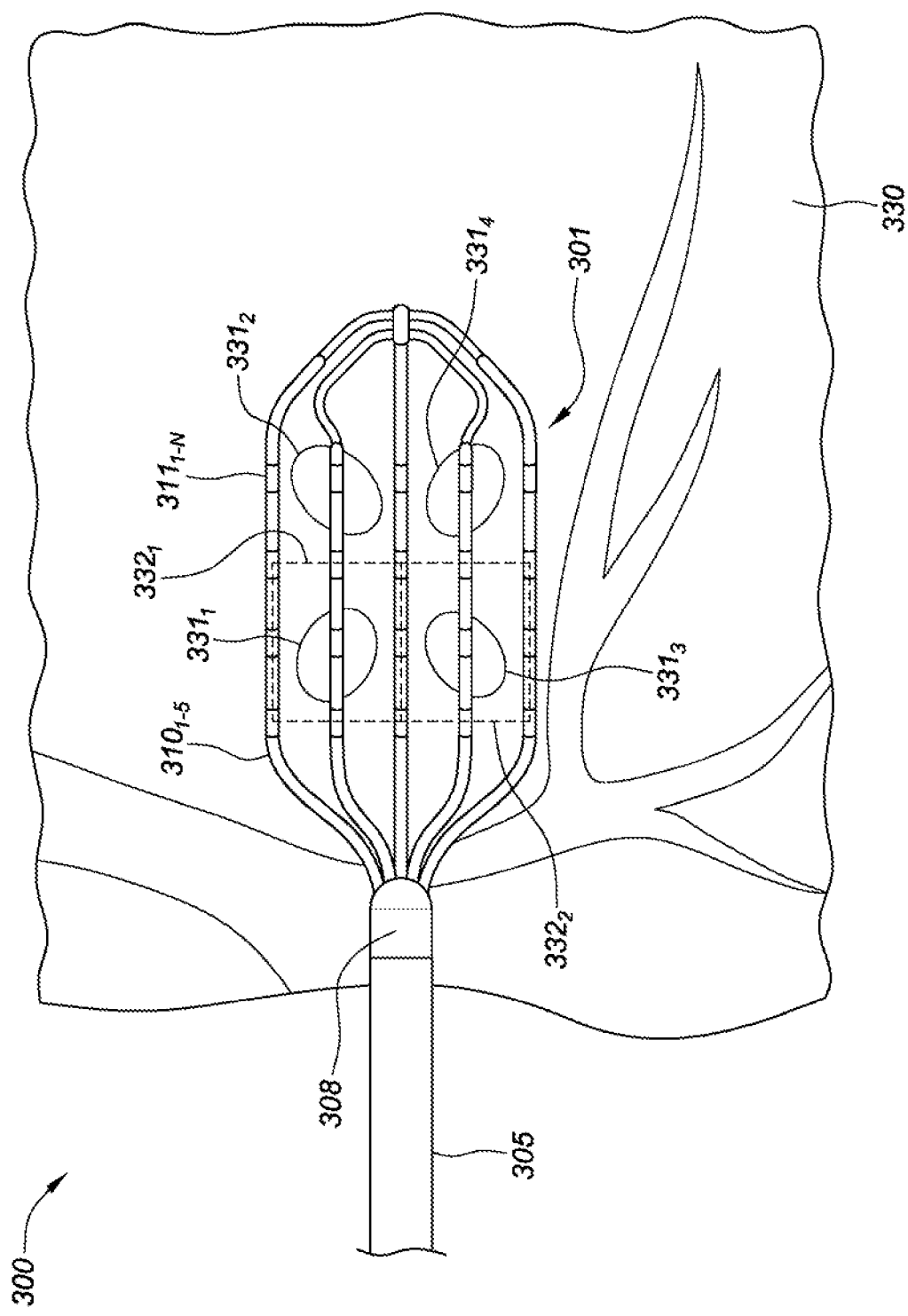
FIG. 3C depicts the planar array catheter of FIG. 3A overlaying vasculature, consistent with various embodiments of the present disclosure.

FIG. 3C depicts the planar array catheter 300 of FIG. 3A overlaying vasculature 330, consistent with various embodiments of the present disclosure. In some embodiments of the present disclosure, the catheter 300 may include steering wires which extend a length of catheter shaft 305. Prior to reaching a bushing 308 that couples the catheter shaft 305 to struts $310_{1-5}$ of planar array 301, the steering wires may be coupled to a pull ring which receives a tension from a proximal end of the steering wires and facilitates steering the catheter shaft 305 and the planar array 301 through a patient's vasculature. As further shown in FIG. 3C, each of the struts $310_{1-5}$ includes a plurality of electrodes $311_{1-N}$ distributed along a length of the struts. In the present embodiment, each of the electrodes are equally spaced. When controller circuitry samples electrical signals from bipole pairs of electrodes within the planar array 301, each of the bipole pairs will detect various electrical characteristics indicative of the tissue health in contact with the electrodes.

In FIG. 3C, vasculature 330 is a left atrium of a cardiac muscle, with the planar array 301 extending across four pulmonary veins $331_{1-4}$. For discussion purposes, an electrophysiology mapping of the patient's left atrium has been completed and a clinician has confirmed the patient's diagnosis of atrial fibrillation. Based upon the electrophysiology mapping taken in proximity to the pulmonary veins 331, the clinician has determined that stray electrical signals are emanating from right superior pulmonary vein $331_1$ and right inferior pulmonary vein $331_3$. Accordingly, the clinician has determined that the right superior and inferior pulmonary veins must be isolated from the left atrium to alleviate the patient's atrial fibrillation symptoms. A plurality of electrodes circumferentially surrounding each of the target pulmonary veins may then be selected and used in either or both mono/bipolar configuration to conduct tissue ablation about the pulmonary veins. The resulting lesions $332_{1-2}$ each surround a respective pulmonary vein and exhibit electrical characteristics which inhibit electrical signal distribution within the left atrium of stray electrical signals from arrhythmic foci within the pulmonary veins.

While aspects of the present disclosure have been presented as being readily applicable to radio-frequency ablation techniques, aspects of the present disclosure are also readily applied to irreversible electroporation (also referred to as direct current ablation). Moreover, while bipolar and monopolar RF techniques have been disclosed herein, variations on such techniques are also envisioned. For example, a bipolar ablation configuration may include alternating adjacent electrode polarities on the electrode array with the ground pad having a negative polarization. In one monopolar ablation configuration, the ground pad may have an alternating polarity over time, with adjacent electrodes carrying alternating polarities. Further, aspects of the present disclosure have been discussed including diagnosis and treatment of cardiac arrhythmias (e.g., atrial fibrillation); however, the present disclosure is readily applicable to the diagnosis and treatment of a number of different ailments, for example, Brugada syndrome.

Yet further embodiments consistent with the present disclosure may be directed to high-voltage direct current ("DC") ablation (either bi-polar or mono-polar configuration). In such embodiments the high-voltage DC may include voltages between 400 and 4,000 Volts, and minimized current draw to target a voltage gradient rather than current delivery.

U.S. provisional application No. 62/414,634, filed 28 Oct. 2016, U.S. provisional application No. 62/572,186, filed 13 Oct. 2017, and U.S. application Ser. No. 15/793,093, filed 25 Oct. 2017 are all generally directed to flexible, high-density mapping catheters and are incorporated by reference as though fully set forth herein.

While various embodiments of high-density electrode catheters are disclosed herein, the teachings of the present disclosure may be readily applied to various other catheter embodiments as disclosed, for example, in the following patents and patent applications which are hereby incorporated by reference: U.S. provisional application No. 61/753,429, filed 16 Jan. 2013; U.S. provisional application No. 60/939,799, filed 23 May 2007; U.S. application Ser. No. 11/853,759 filed 11 Sep. 2007, now U.S. Pat. No. 8,187,267, issued 29 May 2012; U.S. provisional application No. 60/947,791, filed 3 Jul. 2007; U.S. application Ser. No. 12/167,736, filed 3 Jul. 2008, now U.S. Pat. No. 8,206,404, issued 26 Jun. 2012; U.S. application Ser. No. 12/667,338, filed 20 Jan. 2011 (371 date), published as U.S. patent application publication no. US 2011/0118582 A1; U.S. application Ser. No. 12/651,074, filed 31 Dec. 2009, published as U.S. patent application publication no. US 2010/0152731 A1; U.S. application Ser. No. 12/436,977, filed 7 May 2009, published as U.S. patent application publication no. US 2010/0286684 A1; U.S. application Ser. No. 12/723,110, filed 12 Mar. 2010, published as U.S. patent application publication no. US 2010/0174177 A1; U.S. provisional application No. 61/355,242, filed 16 Jun. 2010; U.S. application Ser. No. 12/982,715, filed 30 Dec. 2010, published as U.S. patent application publication no. US 2011/0288392 A1; U.S. application Ser. No. 13/159,446, filed 14 Jun. 2011, published as U.S. patent application publication no. US 2011/0313417 A1; international application no. PCT/US2011/040629, filed 16 Jun. 2011, published as international publication no. WO 2011/159861 A2; U.S. application Ser. No. 13/162,392, filed 16 Jun. 2011, published as U.S. patent application publication no. US 2012/0010490 A1; U.S. application Ser. No. 13/704,619, filed 16 Dec. 2012, which is a national phase of international patent application no. PCT/US2011/040781, filed 16 Jun. 2011, published as international publication no. WO 2011/159955 A1.

Various aspects of the present disclosure may be implemented in conjunction with OIS/OT-like signal processing algorithms for electrophysiology mapping. OIS/OT and related algorithms are discussed in more detail in U.S. provisional application No. 61/944,426, filed 25 Feb. 2014, U.S. application Ser. No. 15/118,522, filed 25 Feb. 2015, and international application no. PCT/US2014/011940, filed 16 Jan. 2014, which are hereby incorporated by referenced as though fully disclosed herein. Yet other embodiments of the present disclosure may be implemented in conjunction with various other algorithm types for electrophysiology mapping. For example, embodiments consistent with the present disclosure may utilize the electrode signal post-processing techniques, and electrophysiology mapping algorithms disclosed in the following publications, which are hereby incorporated by reference: Magtibay et al. JAHA 2017 (J Am Heart Assoc. 2017; 6:e006447. DOI: 10.1161/JAHA.117.006447)(see, e.g., pages 6 and 7, and section titled "Omnipoles Provide the Largest Possible Bipolar Voltages"); and Haldar et al. Circulation AE 2017 (Circ Arrhythm Electrophysiol. 2017; 10:e005018. DOI: 10.1161/CIRCEP.117.005018)(see, e.g., page 6, section titled "Omnipolar Voltage Amplitude Correlates to Largest Measurable Bipolar Vpp," and FIG. 4).

Various embodiments presented herein are amenable to the application of spot electrodes coupled to a flexible electronic circuit, where the flexible electronic circuit may also (partially) comprise the splines and struts of the planar and basket catheters, respectively. Yet other embodiments may be directed to the use of ring electrodes crimped or swaged on to splines and struts, and comprising well-known materials in the art. The ring electrodes being electrically coupled to signal processing circuitry using lead wires. The ring electrodes positioned along the splines and struts form bipole pairs of electrodes with known spacing therebetween. In yet other embodiments, ring electrodes may be swaged or crimped on to a flexible circuit board comprising at least part of the splines, and/or struts of the various catheters disclosed herein.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A planar array catheter comprising:
   an elongated catheter shaft including a proximal end and a distal end, and defining a longitudinal axis;
   a flexible, planar array coupled to the distal end of the elongated catheter shaft, the planar array configured to conform to tissue, and including struts extending substantially parallel with the longitudinal axis, each of the struts lying in a common plane and comprising electrodes coupled thereto, wherein the electrodes are configured to detect electrophysiological characteristics of a contacted tissue in contact with the planar array and operate in a combination of a bipolar configuration and a monopolar configuration to conduct an ablation therapy of the contacted tissue; and
   controller circuitry communicatively coupled to the electrodes and configured to receive signals from the electrodes indicative of the electrophysiological characteristics of the contacted tissue, generate an electrophysiology map of the contacted tissue, operate one or more pairs of the electrodes in the combination of the bipolar configuration and the monopolar configuration based at least in part on the electrophysiology map to ablate a volume of tissue in contact with one of the electrodes of the one or more pairs of the electrodes, and control a depth or width of the ablated volume of tissue using the combination of the bipolar configuration and the monopolar configuration, wherein operation of the planar array in each of the bipolar configuration and the monopolar configuration each comprises applying a voltage differential between 400 and 4,000 volts to produce irreversible electroporation.

2. The planar array catheter of claim 1, wherein:
at least one of the electrodes is a ring electrode that extends circumferentially around one of the struts; and
at least one of the struts comprises a flexible electronic circuit that extends along a length of the strut and is communicatively coupled with one or more of the electrodes supported by the strut.

3. The planar array catheter of claim 1, wherein:
the electrodes comprise one or more spot electrodes; and
at least one of the struts comprises a flexible electronic circuit board that is communicatively and mechanically coupled to at least one of the one or more spot electrodes.

4. The planar array catheter of claim 1, wherein the controller circuitry is configured to identify a pulmonary vein associated with stray electrical signals and control the ablation therapy of the contacted tissue to form an ablation lesion that circumferentially extends about the identified pulmonary vein.

5. The planar array catheter of claim 1, wherein the bipolar configuration includes bipole electrode pairs on adjacent struts of the planar array.

6. The planar array catheter of claim 5, wherein the ablation therapy of the contacted tissue comprises using the bipole electrode pairs to sample electrical characteristics of the contacted tissue and conduct the ablation therapy of the contacted tissue.

7. The planar array catheter of claim 1, wherein the bipolar configuration includes bipole electrode pairs that extend diagonally across adjacent struts of the planar array.

8. The planar array catheter of claim 1, wherein the controller circuitry is further configured to minimize a current supplied to the electrodes and deliver a desired voltage gradient to the contacted tissue.

9. The planar array catheter of claim 1, wherein the controller circuitry is further configured to:
identify one or more pulmonary veins emitting stray electrical signals based upon signals received from the electrodes; and
control the ablation therapy of the tissue to form at least one ablation lesion that circumferentially extends about one of the one or more pulmonary veins to isolate the stray electrical signals.

10. The planar array catheter of claim 1, wherein:
each of the struts comprises a flexible electronic circuit; and
the controller circuitry is communicatively coupled to the electrodes via the flexible electronic circuits.

11. The planar array catheter of claim 1, wherein:
the electrodes are further configured to be operated in the combination of the bipolar configuration and the monopolar configuration to deliver radio frequency energy to the contacted tissue; and
the controller circuitry is configured to control the ablation therapy to vary the depth of the ablation therapy using the combination of the bipolar configuration and the monopolar configuration to deliver radio frequency energy to the contacted tissue.

12. The planar array catheter of claim 1, wherein the controller circuitry is configured to determine a treatment approach used to conduct the ablation therapy of the contacted tissue.

13. The planar array catheter of claim 1, wherein the controller circuitry is further configured to conduct radio frequency ablation in a monopolar configuration using an external ground pad and any one of one or more of the electrodes.

14. The planar array catheter of claim 1, wherein the controller circuitry is configured to control the depth of the ablated volume of tissue to mitigate risk of nerve damage.

15. The planar array catheter of claim 1, wherein the controller circuitry is configured to control the depth of the ablated volume of tissue to compromised myocardial tissue.

16. The planar array catheter of claim 1, wherein the controller circuitry is configured to alternate polarities of two of the one or more pairs of electrodes in combination with an external ground pad having a negative polarization.

17. The planar array catheter of claim 1, wherein the controller circuitry is configured to alternate polarities of two of the one or more pairs of electrodes in combination with an external ground pad having an alternating polarization.

18. A planar array catheter comprising:
an elongated catheter shaft including a proximal end and a distal end, and defining a longitudinal axis;
a flexible, planar array coupled to the distal end of the elongated catheter shaft, the planar array configured to conform to tissue, and including struts extending substantially parallel with the longitudinal axis, each of the struts lying in a common plane and comprising electrodes coupled thereto, wherein the electrodes are configured to detect electrophysiological characteristics of a contacted tissue in contact with the planar array and operate in a combination of a bipolar configuration and a monopolar configuration to conduct an ablation therapy of the contacted tissue; and
controller circuitry communicatively coupled to the electrodes and configured to receive signals from the electrodes indicative of the electrophysiological characteristics of the contacted tissue, generate an electrophysiology map of the contacted tissue, and operate one or more pairs of the electrodes in the combination of the bipolar configuration and the monopolar configuration based at least in part on the electrophysiology map to ablate a volume of tissue in contact with one of the electrodes of the one or more pairs of the electrodes so as to mitigate risk of nerve damage, wherein operation of the planar array in each of the bipolar configuration and the monopolar configuration each comprises applying a voltage differential between 400 and 4,000 volts to produce irreversible electroporation.

* * * * *